US006770068B2

(12) United States Patent
Ruiz et al.

(10) Patent No.: US 6,770,068 B2
(45) Date of Patent: *Aug. 3, 2004

(54) CONTROLLABLE ELECTRO-OPTICAL PATTERNABLE MASK, SYSTEM WITH SAID MASK AND METHOD OF USING THE SAME

(76) Inventors: Antonio Ruiz, Centro Oftalmologico Colombiano, Carrera 20 No. 85-11, Pisos 5o-6o, Santafe de Bogota, D.C. (CO); Eduardo Matallana, Centro Oftalmologico Colombiano, Carrera 20 No. 85-11, Pisos 5o, Santafe de Bogota (CO)

( * ) Notice: Subject to any disclaimer, the term of this patent is extended or adjusted under 35 U.S.C. 154(b) by 10 days.

This patent is subject to a terminal disclaimer.

(21) Appl. No.: 10/207,947

(22) Filed: Jul. 31, 2002

(65) Prior Publication Data

US 2003/0036750 A1 Feb. 20, 2003

Related U.S. Application Data

(63) Continuation of application No. PCT/IB01/01448, filed on Jun. 20, 2001, and a division of application No. 09/598,227, filed on Jun. 21, 2000, now Pat. No. 6,464,692.

(51) Int. Cl.$^7$ ............................................... A61F 9/008
(52) U.S. Cl. .................................. 606/5; 606/4; 349/86
(58) Field of Search .......................... 606/4, 5; 349/86; 372/109

(56) References Cited

U.S. PATENT DOCUMENTS 3,096,767 A    7/1963    Gresser et al.

(List continued on next page.)

FOREIGN PATENT DOCUMENTS

EP    0 417 952 A2    3/1991

(List continued on next page.)

OTHER PUBLICATIONS

"Preparation of Polymer–Dspersed Liquid Crystals", Publication date not known, Pulled from the internet on Jun. 17, 2000, http://abalone.cwru.edu/tutrial/enanced/files/pdlc/prep/prep.htm.

(List continued on next page.)

*Primary Examiner*—Roy D. Gibson
*Assistant Examiner*—Henry M. Johnson
(74) *Attorney, Agent, or Firm*—Smith, Gambrell & Russell, LLP

(57) ABSTRACT

An electro-optical patternable mask is provided which is controllable by way of a processor for presenting a variety of patterns to electromagnetic radiation. In one embodiment of the mask, the electro-optical mask includes an electrochromic layer that works in conjunction with deposited electrode layers (at least one with an x-y pixel array) to present a pattern of non-transmission (colored) and transmission (bleached clear) pixel cells. The sandwiched electrochromic material is supported in one embodiment with a UV grade support substrate with the electrochromic cells of the mask being individually (e.g., individual cells or small groups of individual cells in an array) controlled by a processor and interface to achieve a sequence of different or the same patterns to achieve desired ablation volume upon transmitting ultraviolet energy through the mask such as in conjunction with an opthalmic laser surgery process. In an alternate embodiment a substrate-dispersed liquid crystal material is used in the mask as the means for controlling the transmission of electromagnetic energy such as ultraviolet light of a pulsed laser. An electro-optical device featuring a stacked, preferably monolithic multiple substrate dispersed liquid crystal layer member is also described to ensure blockage of ultraviolet light that hits a pixel cell. The multi-series or multi-stacked substrate dispersed liquid crystal material cell has its field states controlled with electric field generating device which mainains an intermediate substrate-dispersed layer with an electric field across it while the outer substrate dispersed liquid crystal layers can be switched from a no field-blockage mode to an electric-field on full transmission through cell mode. The multi-stack or series electro-optical device is useful as a mask pixel cell as well as in a variety of other field involving wavelength across the visible and ultraviolet spectrum, for example. The various mask embodiments provide a reusable controllable mask well suited for ablation processes such as corneal resurfacing using an opthamological laser surgery (e.g., LASIK) system. The electro-optical mask of the present invention provides for rapid large beam application with a smooth and high precision ablation.

30 Claims, 15 Drawing Sheets

U.S. PATENT DOCUMENTS

| | | | |
|---|---|---|---|
| 4,245,883 A | | 1/1981 | Johnson et al. |
| 4,505,539 A | | 3/1985 | Auracher et al. ........ 350/96.15 |
| 4,605,913 A | | 8/1986 | Pfleiderer et al. ............ 333/166 |
| 4,732,148 A | | 3/1988 | L'Esperance, Jr. ....... 128/303.1 |
| 4,733,369 A | | 3/1988 | Bogner ........................ 365/119 |
| 4,856,513 A | | 8/1989 | Muller .................... 128/303.1 |
| 4,917,486 A | | 4/1990 | Raven et al. |
| 4,994,058 A | | 2/1991 | Raven et al. |
| 5,082,755 A | | 1/1992 | Liu |
| 5,105,215 A | | 4/1992 | Liu |
| 5,207,437 A | | 5/1993 | Miyauchi et al. |
| 5,207,668 A | | 5/1993 | L'Esperance, Jr. |
| 5,208,437 A | * | 5/1993 | Miyauchi et al. ...... 219/121.67 |
| 5,219,343 A | | 6/1993 | L'Esperance, Jr. |
| 5,279,932 A | | 1/1994 | Miyasaka et al. |
| 5,303,709 A | | 4/1994 | Dreher et al. ................ 128/665 |
| 5,312,320 A | | 5/1994 | L'Esperance, Jr. |
| 5,314,422 A | | 5/1994 | Nizzola .......................... 606/5 |
| 5,395,356 A | | 3/1995 | King et al. ..................... 606/4 |
| 5,520,679 A | | 5/1996 | Lin ................................. 606/5 |
| 5,556,395 A | * | 9/1996 | Shimmick et al. ............. 606/4 |
| 5,651,784 A | | 7/1997 | Klopotek |
| 5,703,709 A | * | 12/1997 | Mori et al. .................. 359/196 |
| 5,734,065 A | | 3/1998 | Saika ........................... 549/59 |
| 5,735,843 A | * | 4/1998 | Trokel ............................ 606/5 |
| 5,742,362 A | | 4/1998 | Chikamichi .................... 349/2 |
| 5,747,772 A | | 5/1998 | Matsumura et al. |
| 5,871,879 A | | 2/1999 | Verlinden et al. ........... 430/155 |
| 5,877,833 A | | 3/1999 | Schraivogel et al. ........ 349/149 |
| 5,894,338 A | | 4/1999 | Miehle et al. ............... 351/206 |
| 5,905,590 A | | 5/1999 | Van Der Sluis et al. |
| 5,917,890 A | | 6/1999 | Brotman et al. ......... 379/88.01 |
| 5,928,221 A | | 7/1999 | Sasnett et al. |
| 5,942,136 A | * | 8/1999 | Mori et al. ............. 219/121.68 |
| 5,946,510 A | | 8/1999 | Kobayashi et al. |
| 5,970,187 A | | 10/1999 | Notten et al. ................. 385/16 |
| 5,999,152 A | | 12/1999 | Liao et al. |
| 6,033,075 A | | 3/2000 | Fujieda et al. |
| 6,054,969 A | | 4/2000 | Haisma .......................... 345/7 |
| 6,160,603 A | * | 12/2000 | Tanaka et al. ............... 349/143 |
| 6,184,917 B1 | * | 2/2001 | Chiba et al. ................. 347/256 |
| 6,287,299 B1 | | 9/2001 | Sasnett et al. |
| 6,436,093 B1 | | 8/2002 | Ruiz et al. |
| 6,464,692 B1 | * | 10/2002 | Ruiz et al. ...................... 606/5 |

FOREIGN PATENT DOCUMENTS

| | | |
|---|---|---|
| EP | 0 632 330 | 1/1995 |
| EP | 0 947 158 | 10/1999 |
| WO | WO 91 10170 | 7/1991 |
| WO | WO 98 57604 | 12/1998 |
| WO | WO 99/62397 | 12/1999 |

OTHER PUBLICATIONS

"Application of PDLCs", Publication date not known, Pulled from the internet on Jun. 17, 2000, http://abalone.cwru.edu/tutorial/enhanced/files/pdlc/apps/apps.htm.

"Introduction to Polymer–Dispersed Liquid Crystals", Publication date not known, Pulled from the internet on Jun. 17, 2000, http://abalone.cwru.edu/tutorial/enhanced/files/pdlc/intro/intro.htm.

"Electrochromic Materials and Systems", Publication date not known, Pulled from the internet on May 30, 2000, http://techfac.uni–kiel.de/matwis/ionik/topics/ec.htm.

"Electrochromism", Publication date not known, Pulled from the internet on May 16, 2000, http://plaza.snu.ac.kr/~jncnoy/eca.htm.

"Liquid Crystals Displays", Publication date not known, Pulled from the internet on Jun. 13, 2000, http://stefan.www.media.mit.edu/people/stefan/liquid–crystals/node3.html.

"Super TFT LCD Module", Publication date not known, Pulled from the internet on Jun. 13, 2000, http://www.hitachi.co.jp/Div/mobara/enc/3_2_1.htm.

"Nanocrystalline Electrochromic devices", Publication date not known, Pulled from the internet on May 15, 2000, http://dcwww.epfl.ch/lpi/electr.html.

"Materials, Organic and Ploymer", Publication date not known, pulled from the internet on May 30, 2000, http://www.chem.ufl.edu/_ortega/reynolds.html.

* cited by examiner

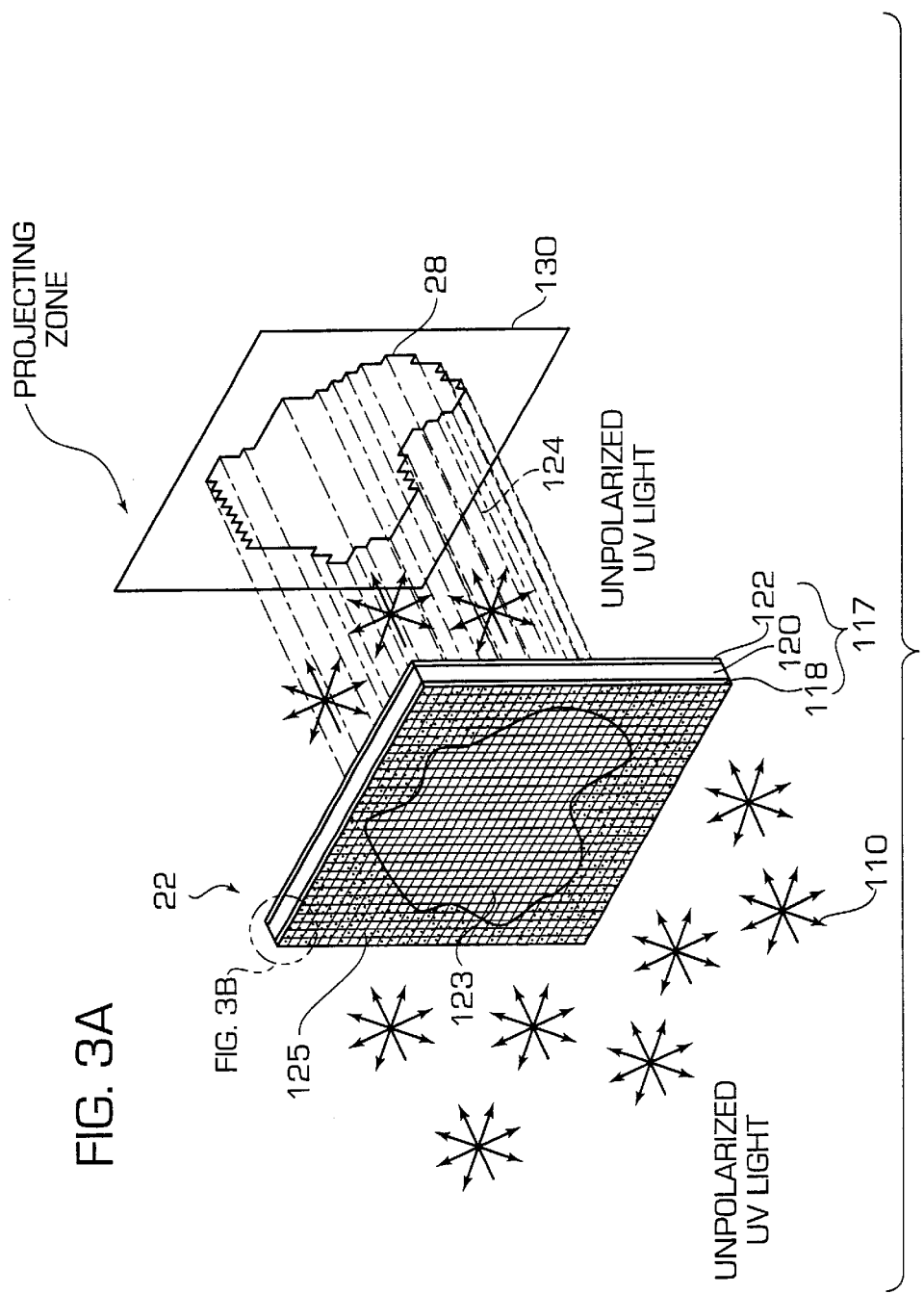
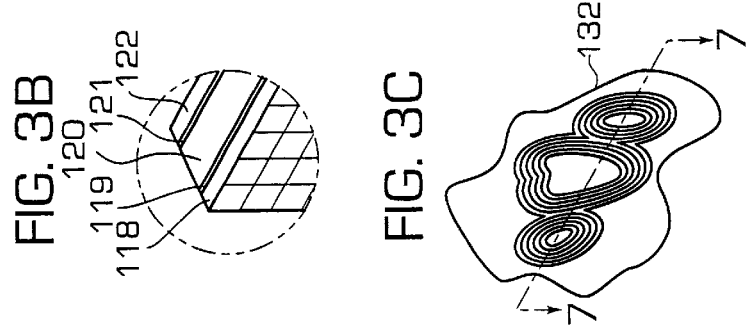

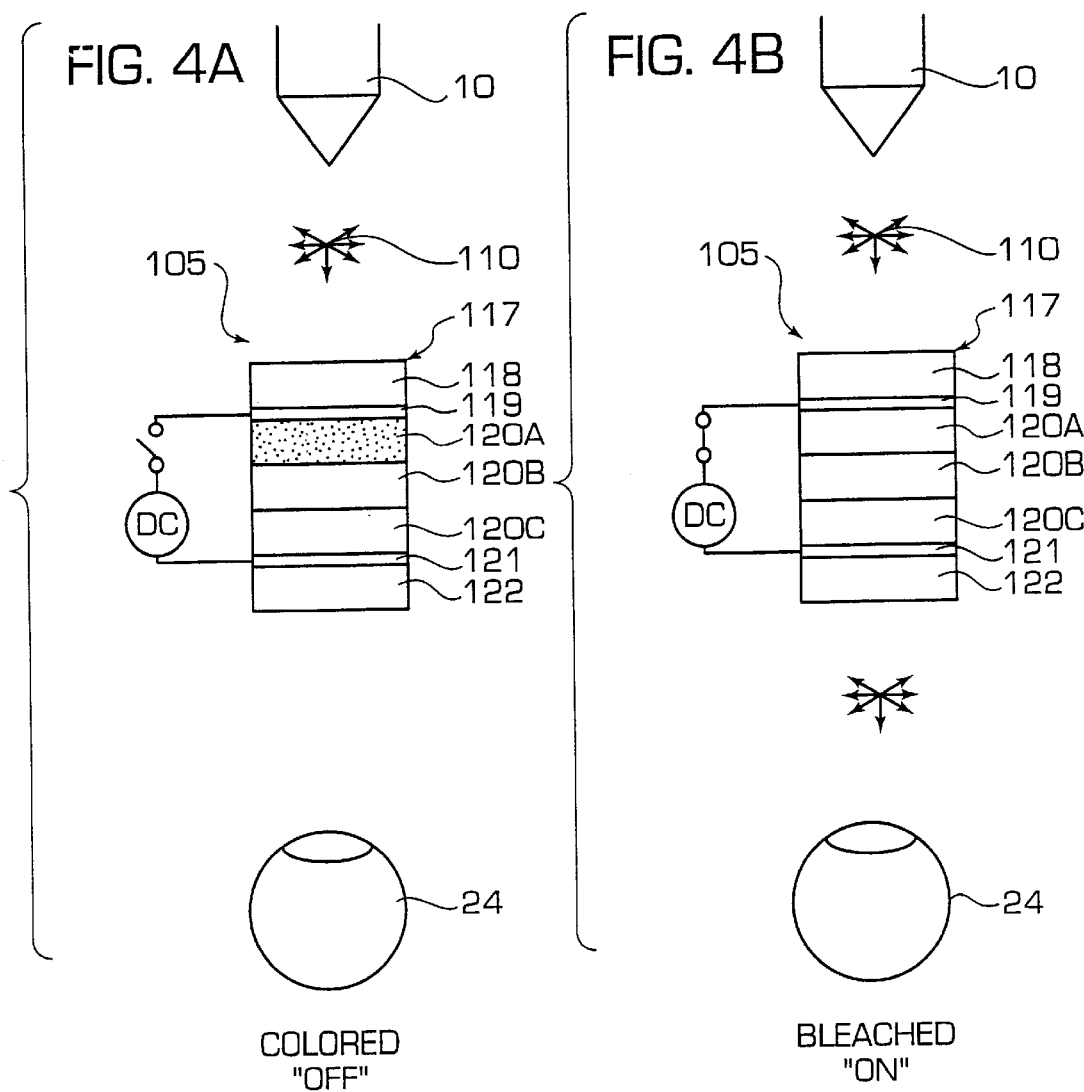
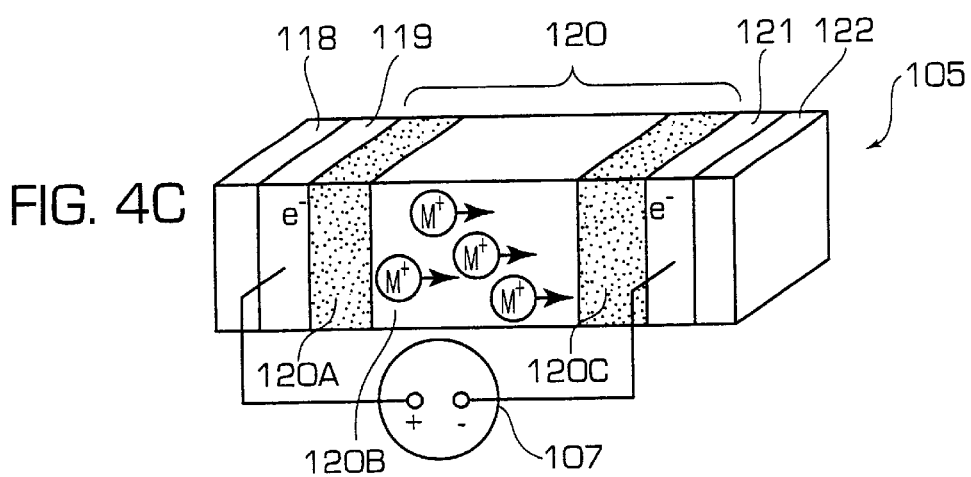

FIG. 4D
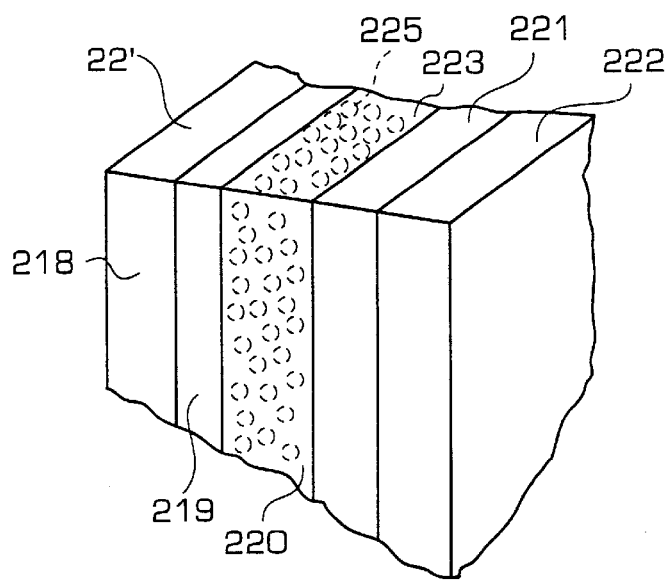
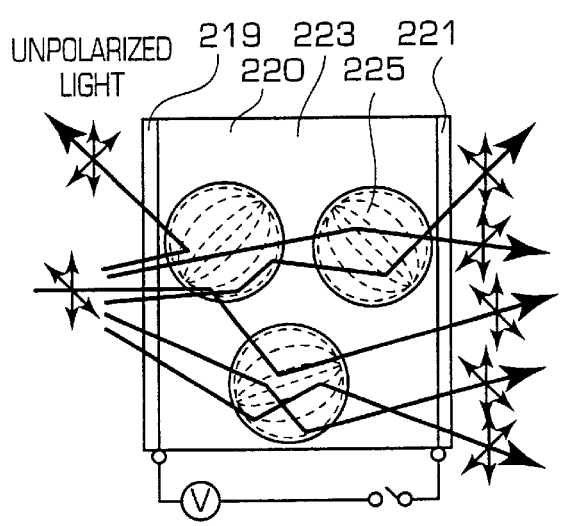
FIG. 4E
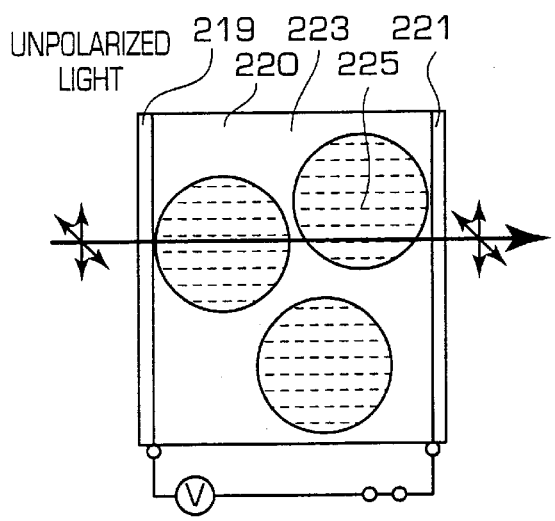
FIG. 4F

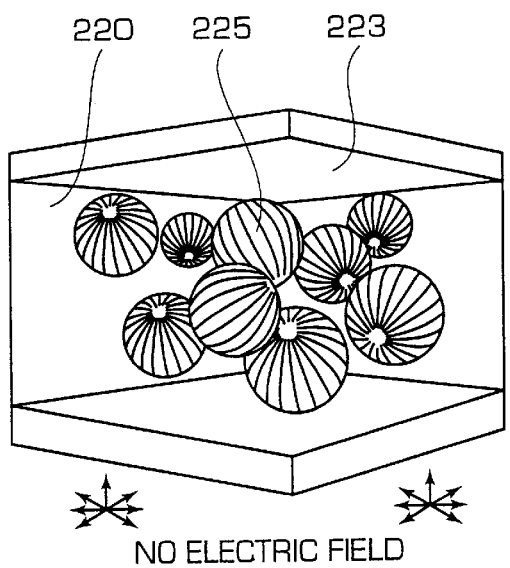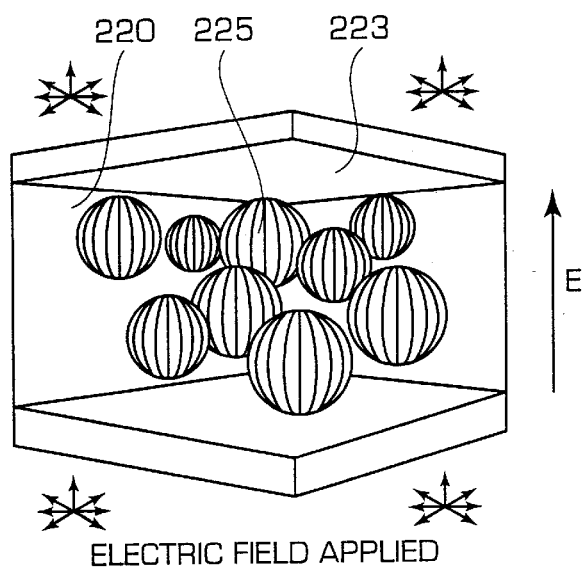
FIG. 4G — NO ELECTRIC FIELD
FIG. 4H — ELECTRIC FIELD APPLIED

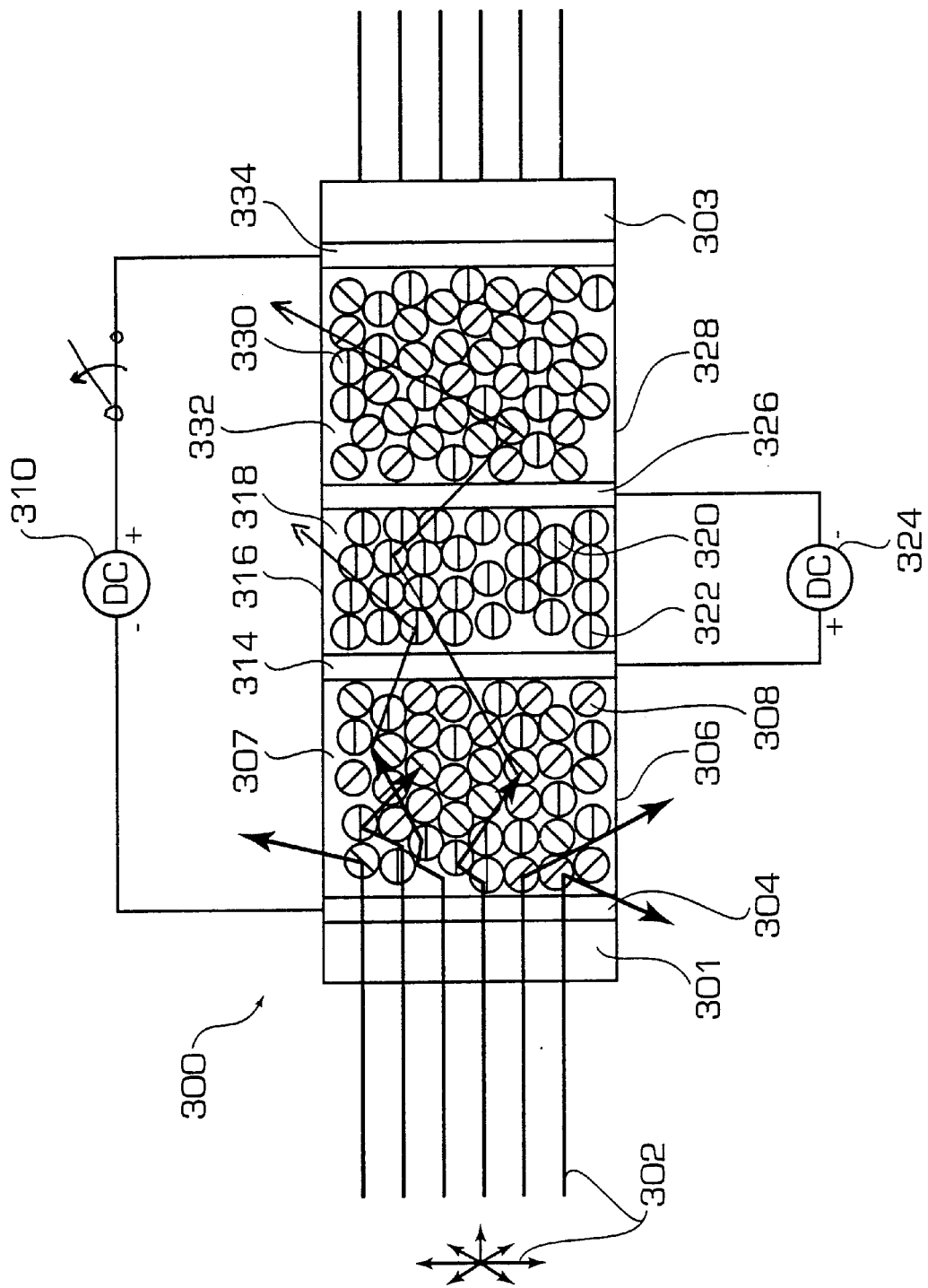

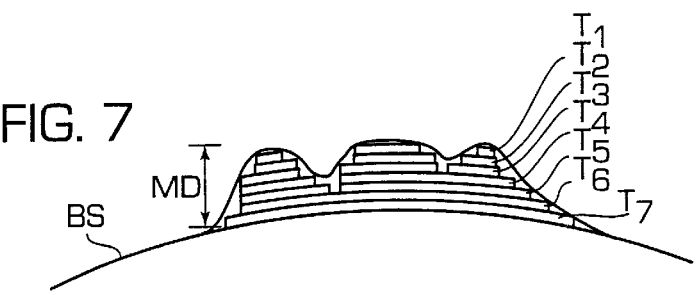
FIG. 7
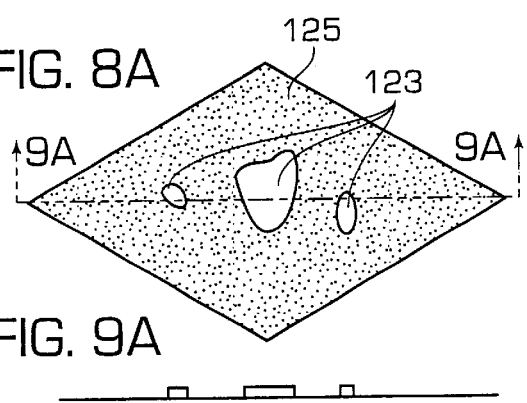
FIG. 8A
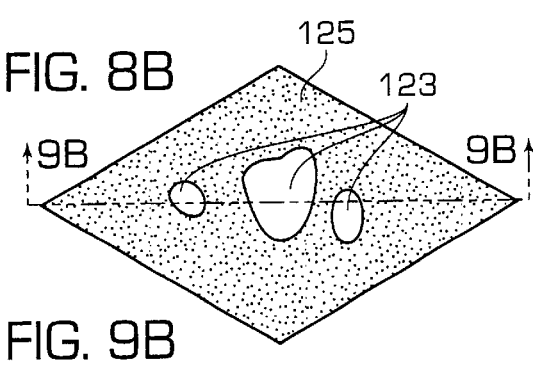
FIG. 8B
FIG. 9A
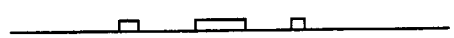
FIG. 9B
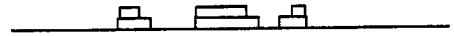
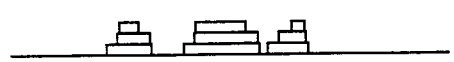
FIG. 8C
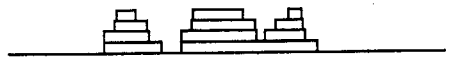
FIG. 8D
FIG. 9C
FIG. 9D
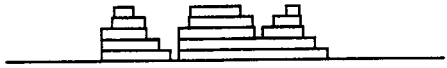
FIG. 8E
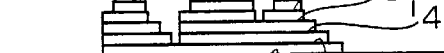
FIG. 8F
FIG. 9E
FIG. 9F FIG. 10
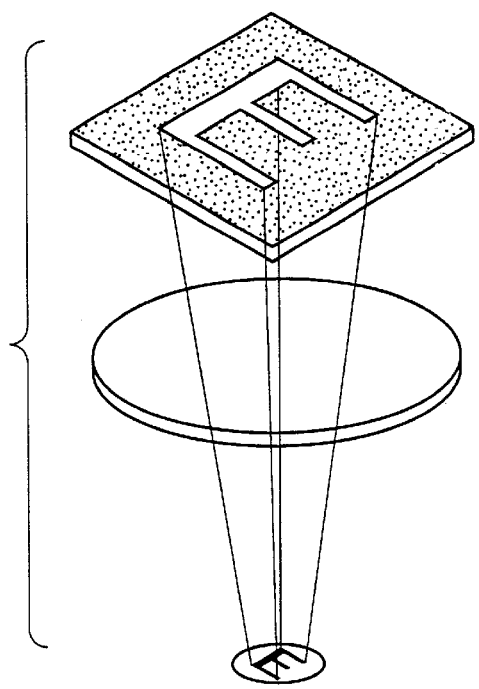

FIG. 11B
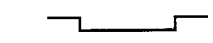
FIG. 12B
FIG. 13B

FIG. 15A LASER PULSE
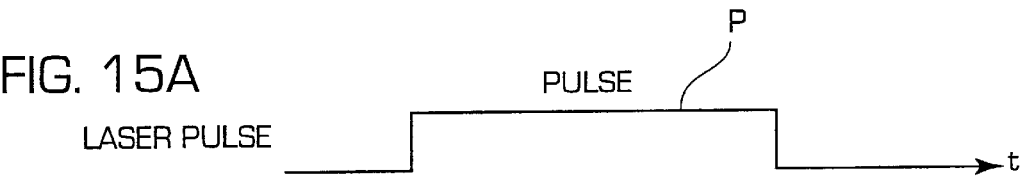
FIG. 15B PIXEL PULSE 100% DUTY CYCLE
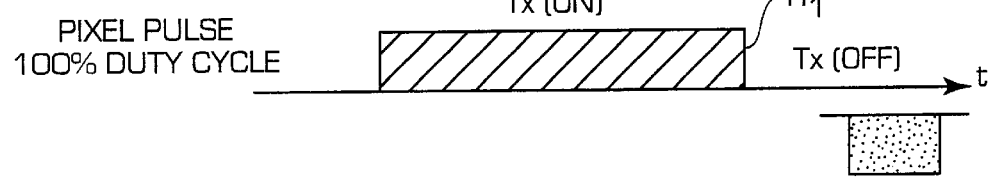
FIG. 15C PIXEL PULSE 50% DUTY CYCLE
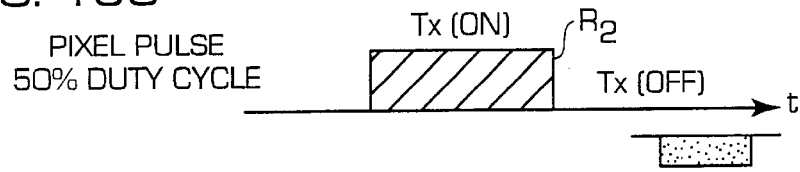
FIG. 15D PIXEL PULSE 25% DUTY CYCLE
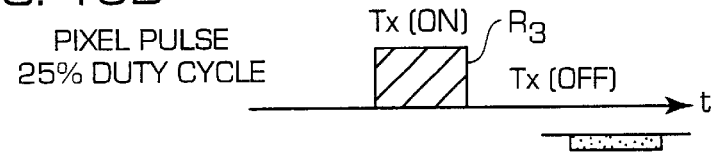
FIG. 15E PIXEL PULSE 12% DUTY CYCLE
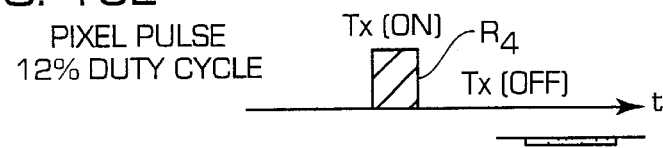
FIG. 15F
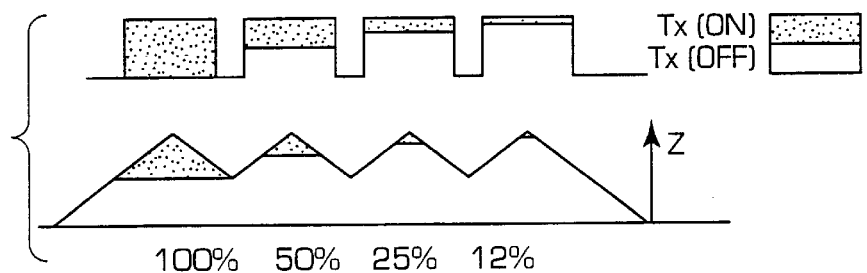

CONTROLLABLE ELECTRO-OPTICAL PATTERNABLE MASK, SYSTEM WITH SAID MASK AND METHOD OF USING THE SAME

CROSS REFERENCE TO RELATED APPLICATIONS

This application is a division of Ser. No. 09/598,227, filed Jun. 21, 2000 now U.S. Pat. No. 6,464,692, and is a continuation of PCT/IB01/01448 having an international filing date of Jun. 20, 2001, and with each being incorporated herein by reference.

FIELD OF THE INVENTION

The present invention relates to a controllable electro-optical patternable mask for controlling electromagnetic energy, particularly an electro-optical mask which utilizes electrochromic or substrate-dispersed liquid crystal cells for transmission control, and a system which involves the use of the controllable mask for use in, for example, an ophthalmic surgical system such as an excimer laser system using ultraviolet electromagnetic energy for contouring the cornea through controlled ablation of the cornea, a photoresist system, a microelectronics system, or a photolithography system, as well as other types of ablation systems.

BACKGROUND OF THE INVENTION

Prior art electrochromic devices are known that include a layer of an electrochromic material, such as $MoO_3$, sandwiched between two transparent electroconductive electrode layers, for example, of indium-tin oxide(ITO). A layer of an H± or Li± ion-conducting material is present between an electrode and the electrochromic material. Electrochromic devices also include devices having an ion-storage layer for storing ions. The application of an electric potential of a few volts across the electrodes causes the color of the layer stack to change. The color change is reversible.

Electro-optical devices containing an electrochromic material layer have been used in conjunction with an anti-dazzling mirror, a light control window and various kinds of display devices as described in U.S. Pat. No. 4,617,619 to Kamimari et al. Electro-optic devices utilizing the electrochromic action (i.e., induced color changes in material such as, e.g., $WO_3$, $MoO_3$ and $V_2O_5$) have also been studied with regard to communication systems using visible or near visible electromagnetic radiation as a message carrier. An example can be seen in U.S. Pat. No. 4,245,883. Reference is also made to U.S. Pat. No. 5,970,187 describing an electrochromic optical switching device and referring to use of the switching devices in rear view mirrors, sun roofs, architectural glass, vision control glass, displays and display screen with variable transmission. These patents are incorporated herein by reference.

U.S. Pat. No. 5,742,362 discloses a process for forming photosensitive material for the manufacture of wiring board which features an exposure apparatus comprising a liquid crystal display for displaying a mask pattern and memory means storing a transmissivity pattern with the transmissivity of each cell of the liquid crystal display element being adjusted in accordance with the transmissivily pattern. Reference is also made to U.S. Pat. No. 5,105,215 entitled "Liquid Crystal Programmable Photoresist Exposure System." These two patents are incorporated by reference.

Electrochromic displays are also known and feature devices that employ a reversible electrochemical reaction to cause a change in color of segments patterned to form alphanumeric characters. Electrochromic displays are passive devices that only modulate ambient light, in contrast to an active liquid crystals that twist ambient polarized light or active light-emitting diode displays that do not modulate light but instead produce light. Hence, the electrochromic displays operate at low voltages, and have a low enough energy requirement that a watch-size display can be operated for about 1 year from a small commercial battery. In the off state, the segments are typically colorless; in the on state, they are brightly colored, for example, blue or purple.

The structure of an electrochromic display package typically consists of two substrate glass pieces, two transparent voltage electrodes, two electrochromic electrodes and one hydrophobic Li electrolyte. All pieces are held together with a solder-glass, or epoxy, seal. To operate the device, a dc potential of 1–1.5 V is applied to the voltage electrodes to activate, the electrochemical electrodes for the electrochromic oxidation and reduction process (redox reaction).

Electrochromic displays can be categorized in two types, bistable, which means that once the color has been switched, the state of the device remains, even in the absence of applied voltage. Limitations of these types of systems includes the slowness of the color change, due to the low migration ratio and the difficulties to obtain strong color changes. In the second type, two complementary electrochromic molecules are dissolved in a solvent. One becomes colored by oxidation and the other by reduction. Thus, this type of system is relatively simple to build, reacts very fast and produces dark colors.

Single layer electro-optical polymer dispersed cells have recently gained attention in the display field and work on the principle of very fine microbubbles trapped into a substrate. When no voltage is applied, the bubbles will take on a random polar orientation. Thus, if a voltage is applied to the cell the bubbles will orientate and align with the electric field, if the substrate carefully matches the index and the director for polarized light of the bubbles, the light will propagate all the way through the material without being reflected at the bubbles and without the need for polarizers.

In the field of laser surgery efforts have been made to ablate an exposed cornea in an effort to achieve a predetermined volumetric ablation pattern to the exposed cornea. In this regard, various surgical techniques for reprofiling of the corneal surface have been proposed as described in, for example, L'Esperance, U.S. Pat. No. 4,732,14; J. T. Lin, U.S. Pat. No. 5,520,679; David F Muller, U.S. Pat. No. 4,856,513; Kristian Hohla, U.S. Pat. No. 5,520,679, these patents are also incorporated by reference herein.

In practice there are two basic techniques to ablate and remove a set volume of tissue in the cornea and they are:

1) a scanning technique that uses a small flying laser spot between 1–2 mm in diameter and requires thousands of pulses to do the surgery; and
2) a large spot beam technique wherein a laser beam of around 8 mm in cross-section is used in conjunction with an erodible mask or a moving, blocking mask to ablate and which generally requires, on average, a few hundred pulses to achieve the desired ablation.

The main advantage of a flying laser spot technique is the ability to readily execute irregular patterns. However, the flying laser spot technique suffers from the drawback of generally requiring longer surgical times to execute the desired ablation pattern both from the standpoint of the number of pulses required and the overlapping requirement to ensure coverage of the ablated area. Any increase in the length of time required to carry out the laser ablation process can lead to longer corneal exposure time and corresponding medical concerns such as cornea dehydration which can lead to poorer healing, poorer visual acuity and, in general, longer post operative recovery times. A longer time period in which a laser is operated per patient also leads to a decrease in the useful life of the laser and an increase in service requirements. Flying laser spot techniques place greater stress on the laser cavity and the optical train components due to high repetition and rate requirements.

A flying laser spot technique also leaves ridges and valleys as a result from overlapping and the resultant ablated surface will not be a highly smooth and polished ablation.

A large beam spot system does allow for more rapid application of the desired energy (including the avoidance of the degree of overlapping involved in a randomly or non-randomly applied, partially overlapping flying spot system) and typically places less strain on the laser equipment, but does not have the irregular pattern versatility provided with a flying spot system. Also, if mechanically moving components are relied upon as the means for blocking or allowing through the laser beam (e.g., an iris or rotating or sliding aperture plate, then the problems of mechanical wear, potential jamming or breakdown arise).

Attempts have been made to provide masks that operate with a large beam application including EP 0 417 952 to Rose et al. which uses a stacked set of binarily weighted masks (A to H) on a cornea intended for sculpturing. A proposed system such as this one suffers from a variety of drawbacks such as the time consumption involved in stacking and developing the mask sets and the increased potential for error brought about by a system using so many different stacked mask components.

Another example of the use of large beam application is found in U.S. Pat. No. 4,994,058 which describes a supported or contact type mask presenting a predetermined resistance to the beam such as through use of a different height erodible mask or by varying the composition of the plastic material making up the mask. A mask arrangement such as this avoids the complications of a scanning laser, but is very limited from the standpoint of having to prepare a new mask for each patient and, with respect to an erodible mask, not having the benefit of being able to test the pattern on a test strip or the like without destroying the mask. In use of an erodible mask there is also heavy reliance on chosen material consistency.

SUMMARY OF THE INVENTION

The present invention is directed at providing a controllable, patternable electro-optical mask which preferably utilizes electrochromic or substrate-dispersed liquid crystal pixel cells for transmission control of ultraviolet electromagnetic energy applied thereto. The mask of the present application has utility in a variety of fields such as use in photo refractive surgery, photoresist systems, microelectronics systems or photolithography systems. The mask is particularly well suited for use with ultraviolet electromagnetic energy utilized in an ophthamological surgical procedure such as a photo refractive keratectomy (PRK); a photo therapeutic karatectomy (PTC); or a laser in-site keratomileusis (LASIK) surgical procedure for resculpturing the exposed cornea of an eye.

Under an ophthamological application, the mask features a controllable electro-optical patternable mask system, an ophthalmic laser surgery system with said controllable mask system, and a method of using the same. The apparatus and method of the present invention is particularly well suited for ablating a corneal surface using a laser in the ultraviolet spectrum and achieves extremely smooth and precise ablation surfaces with a mask system that can be repeatedly used for different patient ablation requirements. The mask is used with a large beam spot (e.g., 6–8 mm) which covers the entire projected surface on a cornea and thus avoids the time delays associated with a flying spot beam as well as ridge and valley formation. In addition to multi-patient use, the present invention avoids the delays associated with the prior art with respect to forming or assembling the mask.

Moreover, the present invention provides a system which can achieve repeated high precision or registration between the planned or predetermined ablation volume to be removed and the actual ablation volume removed so as to enable a surgeon to achieve desired levels of eyesight corrections. Also, the volumetric ablation patterns to be removed can involve highly irregular or regular configurations as an object of the present invention is to provide a system which facilitates the execution of a surgical procedure on highly irregular individual customized patterns on a patient's cornea in addition to more regular volumetric patterns. Furthermore, the electro-optical system of the present invention can be free from the requirement of polarizing. Thus, helping to avoid the drastic 50% power loss of energy when using polarized light, and providing greater flexibility as to the power levels of the ultraviolet electromagnetic source relied upon as there is avoided the power loss which a polarizer can invoke.

The arrangement of the present invention provides a system that can achieve a customized volumetric ablation pattern based on, for example, a stored, ophthamological patient data set (e.g., a volumetric ablation data set as described in U.S. patent application Ser. No. 09/267,926 filed Mar. 10, 1999 by Dr. Luis Ruiz which application is incorporated herein) which data set is developed by a measuring instrument such as a topographer and/or aberrometer. Under the present invention, the volumetric ablation data set is provided to a processor for input to the mask system via a digital interface, for example. The matrix mask system of the present invention includes a mask which receives expanded laser energy and, based on the processed patient data, controls the energy pattern that exits in the mask for sculpturing the desired ablation pattern on the cornea or other substrate being subjected to the ultraviolet electromagnetic energy. In one embodiment of the invention, the mask of the present invention features an electro-optical component having electro-optical material which, in conjunction with other components of the mask, such as electric field generating means, is controllable to produce a pixel pattern to the applied energy so as to control the transmission of energy therethrough, and hence the ablation pattern produced on the projected surface such as the cornea of an eye.

In an alternate embodiment of the invention, the mask comprises a substrate-dispersed liquid crystal material component (e.g., encapsulated liquid-crystal micro-bubbles, within a substrate) which in conjunction with other components of the mask system such as electric field generating means, is controllable to produce a pixel pattern to the applied energy so as to control the transmission of energy therethrough and hence the ablation pattern produced on the projected surface such as the cornea of and eye. Preferably a layered sequence of first electrode layer/first substrate dispersed liquid crystal layer/second electrode layer/second substrate-dispersed liquid crystal layer/third electrode layer/third substrate dispersed liquid crystal layer/and fourth electrode layer (preferably also with outer support substrates) is provided with the orientation of the intermediate substrate-dispersed liquid crystal layer being maintained with an electric field across while the outer (first and third) electrode layers are switched between field off (full blocking mode) and field on (full transmission mode).

The multi sequence substrate-dispersed liquid crystal arrangement described above can be utilized in a variety of other devices in addition to the transmission pixel cell mask described above with a variety of electromagnetic energy spectrum levels including the visible (e.g., as a projector, anti-dazzle, rear view mirror, display device, etc.) in its ability to block and allow through the desired electromagnetic energy by, for example, manipulation of electric field generating means which preferably provides a continuous field across an intermediate substrate-dispersed liquid crystal layer while the outer substrate layers are switched between field "off" and field "on" settings to achieve the desired blocking/non-blocking state.

When ablation is desired with a transmission mask under the present invention, the ablation pattern data set produced is processed by a processor such as the main computer which communicates with the mask via an interface or the like to provide corresponding commands to activate the electro-optical matrix mask. For example, in one embodiment of the invention, the transmission pixel pattern of the mask is individually controlled by the computer and is synchronized with the pulse rate of a main excimer laser. In this way, any regular or irregular ablation volume can be removed by ablating with each pulse of the large beam a set depth (based to the laser characteristics such as laser energy and density) corresponding with the matrix pattern set for that pulse. By changing the matrix pixel pattern with each large beam pulse a different ablation configuration (or the same) can be removed to achieve the desired total pattern, volume and depth.

With an excimer laser working in the ultraviolet energy spectrum, the components of the optical train are subjected to relatively high energy flux levels. In a preferred embodiment of the present invention, a large beam is expanded with a beam expander or the like positioned upstream from the active electro-optical matrix mask to lower the energy density per area received by the pixels of the mask. This avoids premature destruction of the mask. The non-blocked, transmitted portions of the large beam containing the latent image determined by the active mask are then preferably compressed with a focusing lens or the like to achieve the desired ablation profile on the projected surface being ablated.

Thus, the present invention preferably features a controlled ablation of the cornea, using ultraviolet laser radiation to achieve a sculpturing action derived from a computer driving a programmable (preferably digital based) distribution of excimer flux density across an ultraviolet computer controllable electro-optical mask as to achieve a desired volume and shape of ablation for the correction of the curvature of the cornea or for some other application as in the noted photoresist, microelectronics or photolithography fields.

The computer controllable electro-optical mask is based on a matrix array (matrix is used in a broad sense to involve any pattern suited for forming a desired ablation pattern on the ablation plane or surface) of individual electro-optical pixels with optical states between fully transparent to fully opaque or mirror like to the UV light. As noted, the ultraviolet computer controllable electro-optical matrix mask is based on transmission of electromagnetic energy passed through the mask device, with the transmission or non-transmission of light through each individual pixel being preferably controlled by an electrical voltage and a time duty cycle. In one embodiment of the invention the voltage is switched or adjusted to have the pixels either in a fully transparent or fully blocking mode with the pixel switching timing being synchronized with the laser pulse rate. In addition thereto, the frequency duty cycle per pixel can be adjusted or varied with relation to the laser pulse cycle (or with respect to the applied energy in a non-pulse situation) of the main energy source to achieve multiple on and off states of transmission during the main laser pulse cycle (or a set period of applied energy) so as to control the maximum state of ablation during that main pulse (or energy application) cycle from pixel to pixel in the mask.

In one embodiment of the invention, the electro-optical mask is an electrochromic electro-optical mask which features a plurality of controllable electrochromic cells that provide for a patternable mask system for controlling the transmission of electromagnetic radiation therethrough, The plurality of individual pixel cells are individually adjustable to different states of transmission with respect to electromagnetic radiation, and with the pixel cells including electrochromic material. The cells' color states are determined by determining means such as a processor interfaced with said patternable mask for controlling relative transmission states between the individual electrochromic material pixel cells. In one embodiment, the electrochromic material is supported by opposite cell side UV grade support substrates for the passage of UV electromagnetic radiation to the electrochromic material of the pixel cells of said mask The pixel cells are also preferably formed from the outer pair of UV grade substrates, a pair of electrode layers and a solid layer of electrochromic material sandwiched between the electrode layers with the UV grade substrates preferably being a material selected from a group consisting of UV grade synthetic fused silica, sapphire or quartz.

In an alternate embodiment of the invention, a patternable mask system is provided for controlling the transmission of electromagnetic radiation which features a patternable electro-optical mask having a plurality of individual pixel cells with individually adjustable states of transmission with respect to electromagnetic radiation, and said pixel cells including substrate-dispersed liquid crystal material having a substrate material encapsulating dispersed liquid crystal bubbles or droplets. The mask system preferably further comprising a processor interfaced with said patternable mask for controlling relative transmission states between the individual substrate-dispersed liquid crystal material pixel cells.

The substrate dispersed liquid crystal material includes solid encapsulating substrate material (e.g., a polymer) supporting thousands of dispersed liquid-crystal droplets. The mask is also preferably comprised of an outer pair of UV grade support substrates, a pair of electrode layers and an intermediate solid layer of substrate-dispersed liquid crystal material (with the bubbles preferably being less than $5\mu$ in maximum width) with one of the electrodes formed in a pixel array.

In this embodiment, as in the above noted electrochromic embodiment, the UV grade support substrate is preferably a material selected from a group consisting of UV grade synthetic fused silica, quartz and sapphire. The mask system of the present invention preferably further comprises a processor interfaced with said mask for controlling relative transmission states between said individual pixel cells and said processor which comprises means for shifting a pattern formed in said mask in conjunction with a monitored shift in a substrate to receive electromagnetic energy transmitted through said mask.

The present invention also features a mask that comprises pixel cells each with multiple substrate-dispersed liquid crystal material members (preferably solid state layers) with an electrode layer dispersed between said members and to opposite, free sides of the preferably stacked substrate-dispersed liquid crystal material members. In one embodiment, the mask system includes pixel cells having, in series, a first outer support substrate, a first electrode, a first substrate dispersed liquid crystal member, a second electrode, a second substrate-dispersed liquid crystal member, a third electrode, a third substrate-dispersed liquid crystal layer, a fourth electrode, and a second outer support substrate all of which are transparent and assembled as a monolithic unit. This embodiment also preferably includes electric field generating means for maintaining an electric field across said second, intermediate substrate dispersed layer and for switching between an off electric field state for said first and third substrate-dispersed layers and an on electric field state for said first and third substrate-dispersed layers so as to place, in the latter mode state, said first, second and third substrate-disperse layers in a transmission state.

The present invention also features a laser system for ophthamological surgery, comprising a laser and an electro-optical mask having a plurality of individual pixel cells positioned for receiving a laser beam output by said laser with said individual pixel cells having adjustable transmission states for forming a refreshable transmission pattern with respect to the laser beam received from said laser. In one embodiment of the laser system, the pixel cells include an electrochromic component with said electrochromic component being a solid layer of electrochromic material sandwiched between two electrode layers. In an alternate embodiment of the invention, the laser system comprises a mask with pixel cells that include a substrate-dispersed liquid crystal material component with a preferred embodiment featuring a plurality of substrate-dispersed liquid crystal material members arranged in series with respect to a path of laser beam travel.

The laser system also preferably features pixel cells that include first, second and third multiple substrate-dispersed liquid crystal members arranged in a stacked, integral relationship and means for generating an electric comprising means for generating an electric field across said second substrate-dispersed member and means for switching between electric field on and electric field off across each of said first and third substrate dispersed layers while said second substrate dispersed member has an electric field thereacross. The laser system also preferably includes pixel state directing means that includes a processor and an interface linking said processor and mask, and said directing means refreshes a pattern in said mask on a refresh cycle of 100 ms or less. The interface device preferably includes means for converting digital information to individual pixel voltage signals.

The present invention also includes a method for ablating a substrate such as the cornea of an eye which includes directing electromagnetic radiation to a mask having a plurality of controllable, electrochromic or a plurality of one layer or more preferably multi-layer substrate-dispersed pixel cells arranged in a predetermined pattern. The method further includes directing transmitted portions of said electromagnetic radiation exiting said mask onto the substrate for ablating the substrate. In a preferred embodiment the method also includes altering a first pattern defined by said pixel cells into a second pattern between pulses of the laser. In addition the method further features the processing of acquired volumetric ablation pattern data to provide pixel cell transmission state control signals to said pixel cells of said mask. The volumetric ablation data can include that of a cornea of an eye whereby the method includes directing laser beam energy through said mask and onto a cornea of an eye for sculpturing the cornea of an eye. The method of the present invention also preferably includes shifting an ablation pattern formed in said mask to conform to an eyetracker monitored shift in position of an eye being ablated.

The present invention also features an electro-optical device, comprising, in series with respect to electromagnetic radiation travel (e.g., visual or ultraviolet light) a first electrode, a first substrate-dispersed liquid crystal member with the first electrode layer deposited thereon (e.g. a pixel array electrode if used in a transmission mask or some other device wherein individually variable cells are desired or a solid sheet if the entire device is to switch from one state to another as in a window), a second electrode layer, a second substrate dispersed liquid crystal member sandwiching the second electrode layer, a third electrode layer, a third substrate dispersed liquid crystal member sandwiching the third electrode layer in conjunction with the second substrate dispersed liquid crystal member, and a fourth electrode deposited on the free side of the third substrate-dispersed liquid crystal member. The electro-optical device further preferably comprises electric field generating means which maintains an electric field across said second substrate-dispersed liquid crystal member and which provides means for switching between on and off electric field states for said first and third substrate-dispersed liquid crystal members. For example, a first voltage source between the second and third electrode layers and a second independent voltage source connected with the first and fourth electrode layers and switchable between voltage on and off states while the first voltage source maintains an electric field across the second substrate-dispersed liquid crystal member This electro-optical device with its presentment of multiple, controlled layers of substrate-dispersed liquid crystal layers with the control preferably being by way of a maintained voltage application to an intermediate layer and a switched voltage application to the layers external to the more intermediate layer also provides an electro-optical device usable in the visible and ultraviolet spectrum for a wide variety of devices such as those presently being used with electrochromic material.

In one embodiment of the invention, the individually adjustable states of transmission are limited to fully transmitting "on" and fully blocking "off." In another embodiment of the invention, the mask, which is designed for receipt of laser pulses from an excimer laser or the like, further comprises pixel switching timing means for controlling the timing of pixel switching between different on and off states (when desired). In one embodiment, switching takes place in a one-to-one relationship with respect to laser pulses received by the mask. That is, at some time between each pulse, pixel switching activity takes place to alter the pattern presented to the incoming beam of the next pulse.

The mask system of the present invention further includes a pixel switching timing means for timing individual pixel switching between different states and which sets a duty cycle for individual pixels at a duty cycle of from 0% (off for full pulse transmission period) to 100% (on for full transmission period) with at least one or more set pixel duty cycle(s) being at an intermediate value(s) falling between 0 to 100% with respect to the applied or pulse cycle of the main laser beam.

Particularly with electro-optical electrochromic material, it is also possible to change the degree of coloration per pixel by controlling the amount of charge passed through the cell with the degree of color change being fixed upon the switching off of the voltage applied. However, a time based switch over during a particular laser beam pulse cycle with a fixed voltage level can allow for a higher degree of control and is thus more preferable.

The present invention is also directed at a laser system for ophthamological surgery which comprises a laser, and an electro-optical mask having a plurality of individual pixel cells positioned for receiving a laser beam output by the laser. The individual pixel cells of the mask have relatively adjustable transmission states for forming a transmission pattern with respect to the laser beam output by the laser.

The laser system of the present invention further preferably has an expander/collimator assembly that is positioned upstream with respect to the electro-optical mask together with a focusing member positioned downstream from the mask.

The focusing member is designed to focus a latent image pattern formed by the mask onto a projected surface wherein transmitted UV energy of adjacent transmitting pixels is compressed into a minimum overlap relationship (e.g., one involving less than 5% or and more preferably less than 1% overlap) or a minimized spacing relationship (e.g., one involving less that 5% spread apart and more preferably less than 1% spread), or an essentially abutting relationship (of ±0.75% overlap/spacing apart). Preferably the focusing lens is adjustable with respect to the mask and to the focusing plane.

The laser system of the present invention preferably includes directing means for directing pixel transmission state controls to said mask wherein said directing means includes a processor and an interface linking said processor and mask. The processing means preferably further comprises means for processing acquired volumetric ablation volume data and basing pixel control outputs to the mask matrix on the processed acquired volumetric ablation volume data. The laser system also further includes means for acquiring three dimensional volumetric ablation pattern data such as means for receiving corneal ablation data based on topographical and/or aberrometer measurements.

In a preferred embodiment of the invention, the processor further includes means for segmenting acquired corneal volumetric ablation pattern data into a plurality of matrix segments and means for determining a desired individual pixel transmission status arrangement for respective segments of said acquired volumetric ablation pattern. Preferably all processor functions are handled by a central computer in the laser system of the present invention although sub-processor(s) or sub-processor group(s) are also suited for use in the present invention. The system of the present invention also preferably comprises means for sequentially changing a pixel array pattern based on respective, determined pixel transmission statuses for said segments such as a top to bottom or bottom to top sequence with respect to the ablation segments derived from the acquired volumetric ablation pattern data.

The processor of the laser system is in communication with the mask via an interface device such as a digital interface device for converting digital information to individual pixel voltage signals. The laser system of the present invention preferably also includes means for determining a transmission switching rate for individual pixels of said array based on a duty cycle correlated with a laser pulse period of the laser. For example, individual pixels of the mask are assigned one of two states, either a duty cycle of 0% (no transmission) state during the pulse period state or a 100% (full transmission) state during the pulse period state. In an alternate embodiment, at least some of the individual pixels of the mask are assigned a duty cycle that is intermediate the 0% (no-transmission) state during the pulse period and a 100% (full transmission) state during the pulse period.

A preferred embodiment of the laser system further includes an eyetracker and a processing device which is in communication with both the eyetracker and the mask, and the processing device includes means for implementing a switch or changeover in a transmission state of individual pixel shells to shift a pattern defined by pixel cells in said mask form a first pattern position to a second pattern position in correspondence with a shift in location of a projected surface of an eye being monitored by said eyetracker. A similar means can be provided for monitoring and adjusting pixel positions for different types of substrates other than an eye that are subject to movement between laser pulses or refresh states in the mask.

The present invention is also directed at a method for ablating a substrate that comprises directing electromagnetic radiation through an electro-optical mask having a plurality of pixels with individually controllable pixel states, and directing through the electro-optical mask transmitted portions of the electromagnetic radiation onto a substrate such as a corneal surface which receives UV electromagnetic radiation for sculpturing the cornea. The energy is preferably directed through an electro-optical cell that features an electrochromic material to alter the transmission state in a controlled, patterned fashion or through use of a substrate-dispersed liquid crystal material which is preferably a multi-stack of substrate-dispersed layers which block or allow light through depending on the electric field state of the liquid crystal bubbles in each stacked layer.

The method of the present invention further includes altering a first pattern defined by said pixels into a second pattern between pulses of the laser or refreshed states of the mask to alter the ablation pattern on the cornea or exposed substrate. A preferred method of the invention further comprises processing acquired volumetric ablation pattern data to provide pixel transmission state control signals to the individual pixels of the mask. Moreover, the present invention further comprises a method of monitoring any movement of a substrate to be ablated with means for monitoring and, with information obtained from the means for monitoring, shifting the pattern formed in the mask to compensate for a shifting in position of the projected surface prior to the next ablation energy application.

BRIEF DESCRIPTION OF THE DRAWINGS

FIG. 3A illustrates an embodiment of the active electro-optical matrix mask controlling exposure of electromagnetic radiation through a customized irregular pattern on the mask to the projecting zone.

FIG. 3B provides an enlarged view of the active electrochromic matrix mask in FIG. 3A.

FIG. 3C provides a topographical illustration of a volumetric ablation pattern.

FIGS. 4A and 4B provide an electro-optical representation of the on/off transmission states for the electrochromic pixel cell within the active electro-optical matrix mask, with FIG. 4A illustrating the OFF (no transmission) condition and FIG. 4B the ON (transmission) condition of the individual pixel cell.

FIG. 4C provides an enlarged view of the preferred first embodiment for the electrochromic pixel cell.

FIG. 4D provides an enlarged view of the preferred second embodiment of the active matrix mask when the cell is from an electric field controlled substrate-dispersed liquid crystal matrix mask.

FIG. 4E illustrates unpolarized light when interacting with random orientated micro-bubbles on a single substrate-dispersed liquid crystal cell.

FIG. 4F illustrates unpolarized light that is transmitting through the mask cell made possible by the aligned micro-bubbles upon the application of a small voltage to a single substrate-dispersed cell.

FIGS. 4G and 4H further illustrate the effect on the orientation of the micro-bubbles when aligned by an electric field, on a single electric field controlled substrate-dispersed cell.

FIG. 4I illustrates unpolarized light interacting with random orientated micro-bubbles of a triple stack substrate-dispersed liquid crystal while in a non-transmission full block state

FIG. 7 shows a crossectional view through a cornea of a patient having an irregular topography, a schematic depiction of a best clinical sphere lying below the lower extremities of the irregular surface, and the cumulative ablation volume removed by way of a plurality of laser pulse transmission through different patterns provided in the electro-optical active mask.

FIGS. 8A to 8F each provide a schematic illustration of six different patterns formed in the active electro-optical matrix mask in sequence and between laser pulse applications.

FIGS. 9A to 9F show a crossectional view of the volumetric ablation volume segment (corresponding to the matrix segment generated by the process) being removed upon transmission of a laser pulse (or a common number of pulses) with FIGS. 9B–9F showing the cumulative ablation.

FIG. 10 shows a schematic view of the UV light beam exiting the active mask and being focused and the corresponding ablation pattern (the letter "E", representing the pattern to be ablated with respect to a projecting surface).

FIG. 11B shows the ablation layer cross-section pattern along cross-section lines 11B—11B in FIG. 11A and the intermediate non-ablated with the non-formed registration between the focused transmitted energy and the projecting surface.

FIG. 12B shows the ablation layer cross-section pattern along cross-section line 12B—12B in FIG. 12A, showing the smooth perfect ablation.

FIG. 15A shows a time based depiction of a main laser's pulse.

FIG. 15B shows a time based depiction of a full "on" pixel transmission relationship with respect to the main laser pulse without intermediate states and at a 100% duty cycle.

FIG. 15C shows a time based transmission "on" setting for the switching between a first pixel state (overall or individual) and a second pixel state with the switched pixels being at a 50% duty cycle with respect to the main laser pulse period.

FIG. 15D shows a different (25%) duty cycle for the switching between pixel states (individual or overall) with respect to the main laser pulse period.

FIG. 15E shows a (12.5%) duty cycle for the switching between pixel states (individual or overall) with respect to the main laser pulse period.

FIG. 15F illustrates the relationship between a pixel provided with different duty cycle states and the relationship with the corresponding ablation.

DETAILED DESCRIPTION OF THE PREFERRED EMBODIMENTS

Figure 1:
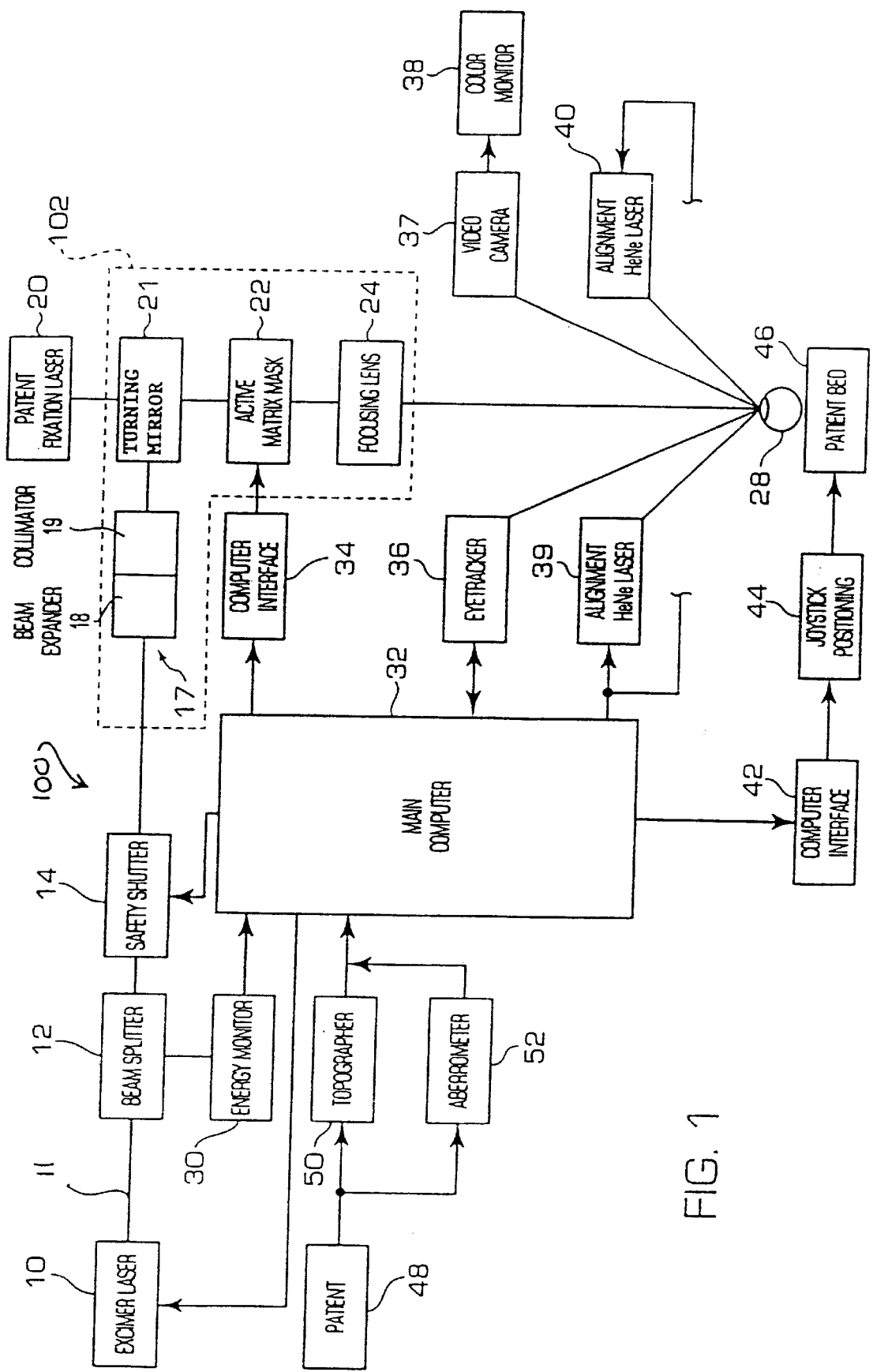
FIG. 1 is a general block diagram of a representative embodiment of the present invention in the form of an ophthalmic laser surgery system with controllable electro-optical matrix mask system utilized therein.
Figure 2:
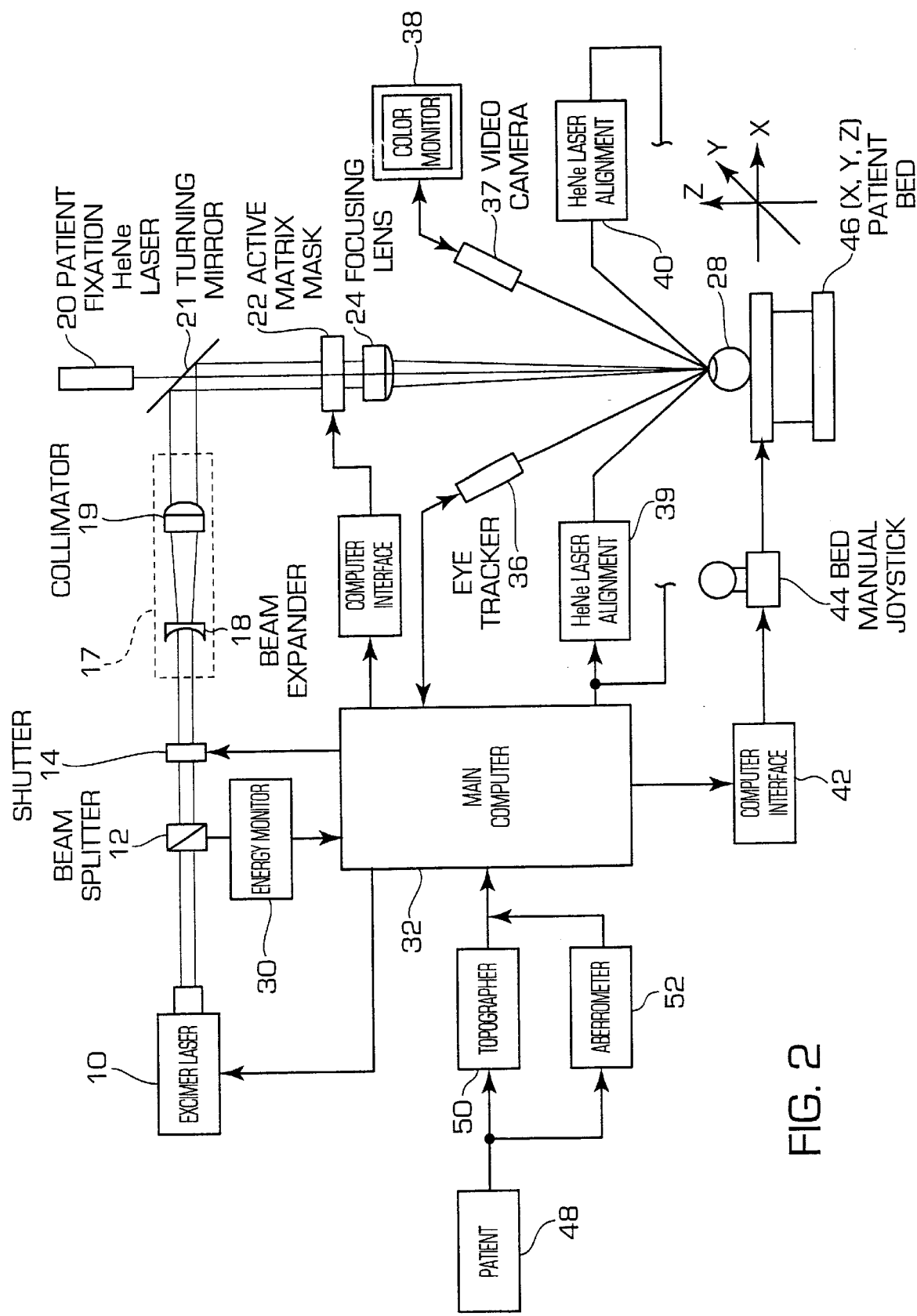
FIG. 2 is a general, schematic physical diagram of the ophthalmic laser surgery system of FIG. 1.

FIG. 1 shows a block diagram of one preferred embodiment of a laser system of the present invention which includes an electro-optical active mask of the present invention. The block diagram in FIG. 1 illustrates an opthalmic laser surgery system 100 of the present invention, and FIG. 2 provides a schematic physical presentation of that which is shown in FIG. 1. As shown in FIGS. 1 and 2, a laser beam is delivered by laser 10, which is preferably an excimer laser outputting ultraviolet light at a wavelength of 193 nm, although other ultraviolet energy levels suited for ablating corneal tissue can be relied upon in the system shown in FIG. 1.

The laser beam outputted by excimer laser 10 is a large spot laser beam such as, for example, that provided by a Lambda Compex Model 205 excimer laser manufactured by Lambda Physics GmbH, located in Gottinggen, Germany from which there can be generated a circular beam with a diameter of 6 to 10 mm (which is well suited for accommodating most eye configurations) and outputs a pulse in excess of 400 mj which is sufficient for corneal ablation. An 8 mm diameter large beam with an energy level of 400 mj or higher is particularly well suited for the preferred applications of the present invention.

The large spot beam 11 output by the laser is passed through a beam splitter 12 where a small quantity of the UV light is reflected by the beam splitter to be input and measured by the energy monitor 30. The energy monitor 30 then inputs the monitored energy information to main computer or main processor 32 where a comparison is made between the actual energy being output by the laser and the desired energy level, and the processor directs an adjustment signal to the laser's voltage source to effect any adjustments needed to obtain the desired energy level at the laser head to maintain a constant energy level.

The UV light passing through the beam splitter is directed to safety shutter 14 preferably in the form of a mechanical, physical light beam blocking device. The safety shutter is placed "on" when the system is in surgical mode and is placed "off" in a blocking position whenever the processor receives an input from one of the laser system's components suggesting a device is not working within established parameters or upon an operator's activation of an emergency shut off.

During a non-shut off state of operation, the UV light beam 11 is directed to beam expander/collimator assembly 17 which includes beam expander 18 and collimator 19. Beam expander 18 provides a beam expansion function while collimator 19 functions to limit the degree of expansion to a predetermined level. Under the present invention, the beam expander/collimator assembly distributes and lowers the energy density per area of the large beam 11 prior to the expanded beam being applied to the active electro-optical matrix mask 22. Because UV light energy at the typical wavelength suited for corneal ablations (e.g., 193 nm) has relatively high energy levels, the expansion is helpful in prolonging the life of the electro-optical matrix mask 22 embodiments of which are described in greater detail below.

The resulting expanded light is preferably reflected or redirected (due to the typical positioning of the laser head) by turning mirror 21 so as to travel in a straight line to the projecting zone or surface 28 (e.g., exposed corneal surface being ablated).

The light beam is then directed to the active electro-optical matrix mask 22 which has a controllable, refreshable multi-use pixel array with each pixel preferably being individually controlled to vary the light beam transmission characteristics of each pixel.

FIG. 1 also shows, by way of dashed lines a preferred controllable patternable electro-optical transmission mask system 102 which comprises, in the illustrated embodiment, beam expander/collimator assembly 17, turning mirror 21, electro-optical matrix mask 22, and focusing lens 24.

FIG. 3A shows in greater detail controllable electro-optical mask 22 (an electrochromic cell in this instance although also generally representative of the layer location of a single layer substrate-dispersed liquid crystal cell).

In FIG. 3A the unpolarized light beam from the excimer laser is directed at active electro-optical matrix mask 22.

FIGS. 3A, 3B, 4A, 4B, 4C, 5 and 6 illustrate a preferred embodiment of an electro-optical active mask 22 of the present invention.

Figure 5:
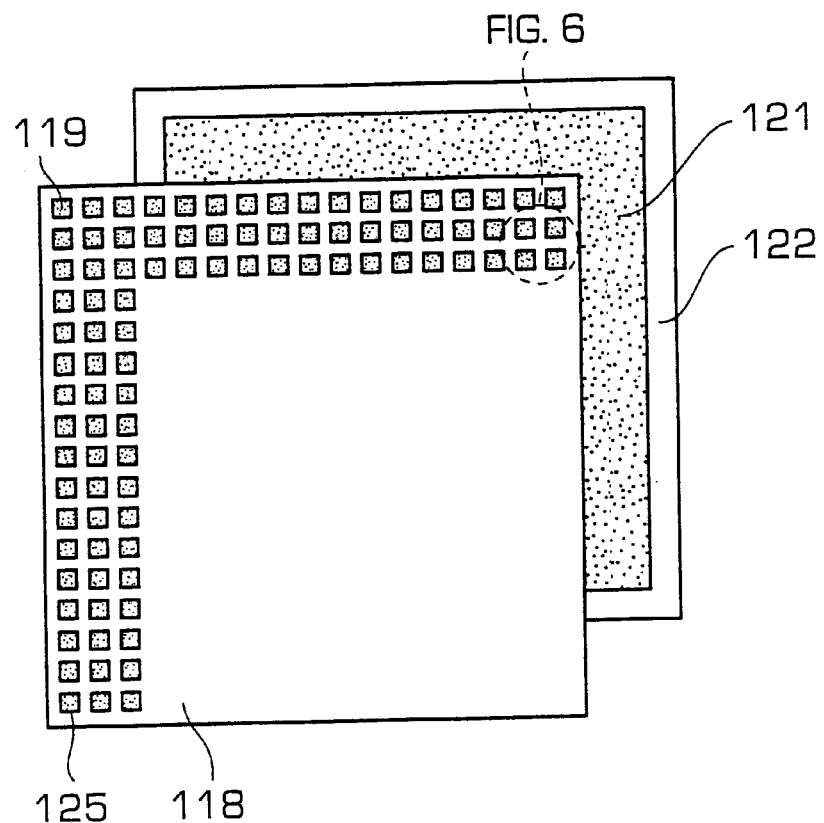
FIG. 5 shows an exploded view of a portion of the active electro-optical mask shown, for example, in FIG. 3A with the normally transparent electrode pixels being darkened to facilitate an explanation thereof.
Figure 6:
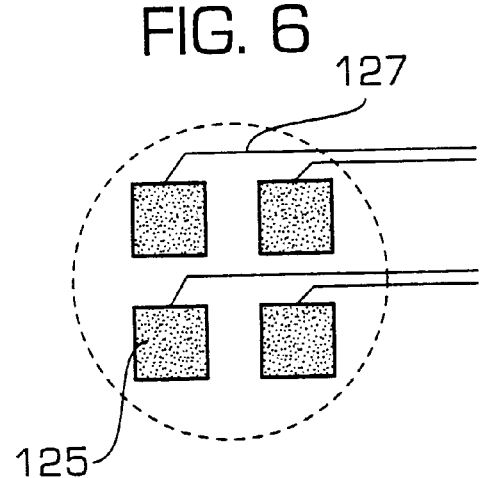
FIG. 6 shows an enlarged view of the circled segment in FIG. 5.
Figure 11A:
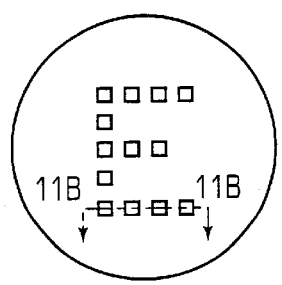
FIG. 11A shows a close up view of the ultraviolet energy application in FIG. 10 on the cornea with the transmitted energy from the spaced apart pixels of the matrix being placed in a spaced apart arrangement on the ablation plane or projected surface.
Figure 12A:
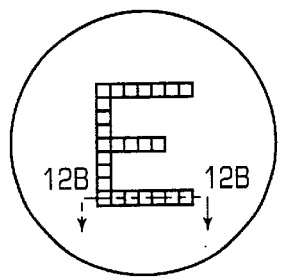
FIG. 12A shows the ablation pattern provided on the projected surface with the individual pixels forming a non-overlapping, non-spaced (abutting) ablation.
Figure 13A:
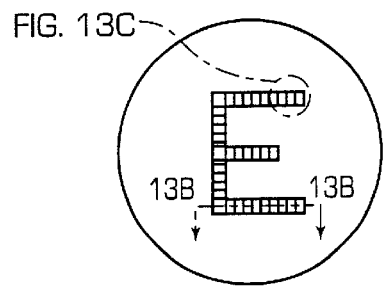
FIG. 13A shows an excess overlap arrangement in the ablation pattern imposed on the substrate.
Figure 13C:
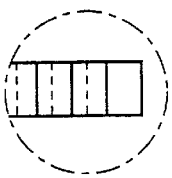
FIG. 13B shows the ablation layer cross-section pattern along cross-section lines 13B—13B in FIG. 13A showing spikes formed by over-ablation registration caused by overlapping the focused transmitted energy with respect to the projecting surface.

FIGS. 3A and 3B shows an illustration of the electro-optical electrochromic mask 22 comprising a multi-layer assembly 117 which includes first substrate plate 118 of, for example, UV grade synthetic fused silica (i.e., UVGSFS ($SiO_2$)). This transparent substrate plate is followed by a first, transparent voltage electrode layer 119, followed by the electrochromic cell 120, which itself is preferably comprised of a multi-layer assembly which comprises 120A (FIG. 4A) representing a first electrochromic electrode, 120B representing a solid state electrolyte, and 120C representing a second counter electrode. One of the electric field generating electrode layers (119, 121) connected to the dc voltage source has the pixel electrode cells 125 (typically deposited and shown in FIGS. 5 and 6) and the (typically deposited) voltage lead lines 127 (FIGS. 5 and 6). In the illustrated embodiment, first electrode 119 has the pixels array while a second voltage or electric field generating electrode layer (e.g., a deposited ITO layer) 121 is sandwiched between counter electrode 120C of the electrochromic component 120 and second support substrate 122 having similar properties to first support substrate 118.

Electro-optical element 120 is provided between first transparent electrode layer 119 and second transparent electrode layer 121, with the second electrode 121 layer in the illustrated embodiment being a full sheet electrode layer (with a generally matching peripheral relationship with respect to the pixel electrode cells 125 outer peripheral border). Thus, upon application of a low level voltage (on or off or of opposite polarity) to the electrodes (depending on the preferred, preset condition) on each predetermined individual pixel cell, a desired pixel mode can be achieved due to a change in the transmission state of the electro-optical material associated with the activated pixel. Preferably, the deposited 119 electrode layer is deposited directly on the substrate 118 as a thin layer of (ITO) indium-tin oxide or $SnO_2$ by means of conventional depositing techniques such as vacuum evaporation, chemical vapor deposition, electroplating, or other commonly known methods.

As shown in FIGS. 5 and 6, the pixel cells (only some shown for draftsman convenience) are preferably arranged in a square matrix which is sufficient in number to achieve the desired degree of ablation precision such as a 1024×1024 pixel array with a pixel size of 100$\mu$ or less being preferred, although other resolutions are also possible such as lesser number pixel arrays (e.g., 512×512) and larger pixel sizes (e.g., 100$\mu$ to 150$\mu$). In FIG. 5, the deposited electrode material is shown darkened to facilitate explanation, although the material is transparent in a preferred matrix embodiment. Thus, in FIG. 5 the pixels defined by the pertinent pixel electrode material is visible through the transparent substrate 118. The electro-optical layer which is normally sealed between the sandwiching electrode layers is also not shown in FIG. 5.

FIG. 3A further illustrates irregular pixel latent pattern 123 formed in active matrix 22 which is differentiated by the lighter shaded pixel area 123 in the mask (transparent-transmission state) and the darker shaded pixel area 125 (non-transparent non-transmission). For illustrative purposes, there is provided in FIG. 3C, the total volumetric ablation pattern 132 with the three dimensional topography associated with the irregular pixel pattern 123. Each topography level representation preferably corresponds to a single volumetric ablation segment of the entire ablation volume (shown schematically as each ablation segment would, in a preferred embodiment, correspond with the ablation depth characteristic of the laser which, for a full duty cycle, is often around 0.21$\mu$ to 0.25$\mu$).

The electrical optical mask of the present invention can take on a variety of forms. In one embodiment of the invention the electric-optic cell is an electrochromic type and in another embodiment the electric-optic cell is a substrate-dispersed liquid crystal cell, such as a polymer dispersed liquid crystal cell. In any event, the optical shutter means is placed between two external electrodes defining each individual pixel cell. In this way, an electro-optical cell is made available to obstruct the electromagnetic energy such as the pulsed ultraviolet excimer laser beam (normally off) or to transmit light (normally on). In a preferred embodiment unpolarized excimer UV light is directed to the mask 22 comprising many individual adjustable electro-optical pixel cells that are individually controllable to form the desired ablation pattern.

When no voltage is applied, the incoming light is obstructed by each normally off state of the individual pixel by way of its proper transmission modes as represented by the darkened areas in the mask pixel array 125 in FIG. 3A. Then when a voltage is applied across the desired electrodes, the affected pixel cells become transparent as represented by the transmission state pixel cell pattern.

FIG. 4A and 4B illustrate schematically the relationship wherein excimer laser 10 is directing unpolarized light 110 to the electro-optical cell 105 (forming one on of many pixel cells in active mask 22). In FIG. 4A the voltage source is off such that the electro-optical cell 105 is in a non-transmitting or off mode. The electromagnetic energy 110 (e.g. UV light) coming form the excimer laser head 10 is oscillating in all directions and then goes to the electro-optical matrix mask but it can not pass through if no voltage is applied across the electrode layers. Accordingly, in the transmission pixel cell state when voltage is applied in FIG. 4B light is exposed onto the projecting zone as the pixel is in a bleached state.

FIG. 4C provides a schematic presentation of the electro-optical properties of the electrochromic cell 105 contained in mask 22 which has all of its components transparent when the cell is in an uncolored state. As shown in FIG. 4C, the electrochromic cell 105 features outer support substrates 118, 122, with each being a UV grade substrate such as fused silica, sapphire or quartz when the electromagnetic energy is in the non visible, ultraviolet spectrum. As represented in FIG. 4C, an electric field producer 107 is in electrical communication with deposited electrode sheets 119 and 121 with the segment of sheet 119 in FIG. 4C representing a pixel segment of sheet 119. By passing a current through the cell through use of electric field generator 107, the coloration of the cell can be achieved and, hence the absorption quality of the cell with respect to incoming electromagnetic energy. The degree of coloration can be controlled by the amount of charge passed through the cell and for a bistable electrochromic material the color state remains after switching off the voltage. To bleach the device, the polarity across the cell is reversed via the electric field generator.

With respect to an electro-optical mask, such as mask 22 used with ultraviolet electromagnetic radiation (preferably 193 nm) laser surgery system 100 in FIG. 1 (or other electro-optical devices involving different electromagnetic spectrum levels as explained below), reference is made to FIGS. 4D to 4H which illustrate an alternate electro-optical mask system of the present invention featuring a substrate-dispersed liquid crystal material component for establishing different transmission states amongst a plurality of mask pixels preferably arranged in a matrix (e.g., 1024×1024 in number with a pixel size of 100$\mu$ or less) and connected with a processor for controlling the transmission status to achieve a desired energy transmission patterns in the mask. As in the previously described embodiment, each pixel cell in the mask is preferably individually and activity controlled to change the transmission state (when desired) to achieve, in the cumulative, the desired pattern to be presented to incoming energy such as large spot beam, pulsed ultraviolet electromagnetic radiation from an excimer laser on the like such that the mask can be used to control the pattern ablated in an underlying substrate.

FIG. 4D provides a cut-away view of a segment of an alternate embodiment of an electro-optical mask such as active mask 22 shown in FIG. 1. The electro-optical mask segment shown in FIG. 4D features an alternate means for varying the transmission state of the pixel cells provided in active patternable transmission mask 22 which includes a substrate-dispersed liquid crystal component 220 (typically a thin layer of the substrate having dispersed throughout bubbles or drops of liquid crystal material). The active mask (noted 22' in FIG. 4D) represented by the segment illustrated in FIG. 4D features a plurality of pixel cells (preferably defined by pixel shaped electrode segments formed in one or both of the electrode layers of the mask) as described above and shown in FIG. 5 and 6.

FIG. 4D illustrates the mask 22' as comprising an outer support substrate 218 on which is deposited electrode layer 219 (preferably with "pixel" electrode segments) in one of the conventional depositing methods. Another electrode layer (preferably continuous without "pixel" electrode segments) 221 is preferably deposited on the opposite side support substrate 222. Between the two substrate/electrode layers is sandwiched substrate-dispersed liquid crystal component 220.

As in the earlier described embodiment when the mask is to be subjected to ultraviolet energy such as in the laser system illustrated in FIG. 1, the components making up the mask 22' are made of UV grade material so as to accommodate and not block out the UV waves when it is desired that the pixel cell is to be in a transmission mode for allowing the patterned energy formed by the mask to form a predetermined ablation in the substrate.

As represented in FIG. 4D, substrate-dispersed liquid crystal layer 220 is formed of an encapsulating substrate material designed for the intended electromagnetic radiation energy levels to be imposed on the mask. Dispersed within the substrate is a large number of liquid crystal droplets 225 which fill up (or at least partially fill up) holes in the dispersion substrate 223. The droplets, in addition to being distributed throughout the desired active mask region of mask 22' are preferably less than 5$\mu$ across.

The dispersion of the droplets in the substrate can be formed, for example, by microencapsulation wherein the substrate (e.g., a polymer) while in a fluid state with water, is mixed with liquid crystal material and the water evaporated out. By evaporating out the water thousands of tiny "capsules" with liquid crystal material in them are formed within the substrate.

A phase separation process can also be relied upon to form the tiny droplets of liquid crystal material such as by way of, for example, a substrate-induced phase separation, a thermally-induced phase separation and solvent induced phase separation. Substrate induced separation involves the mixing of a liquid crystal with the substrate in solution (non-solidified) form. A reaction process is then initiated with, for example, the introduction of a catalyst material. As the reaction progresses, the liquid crystal molecules come out of the solution and form droplets as the encapsulating substrate solidifies therearound.

In a thermally-induced phase separation the substrate, which has a melting temperature below its decomposition temperature, a homogeneous mixture of the liquid crystal and melted, encapsulating substrate is formed. The mixture is then cooled to induce phase separation whereupon liquid crystal droplets begin to form as the encapsulating substrate hardens.

In a solvent-induced phase separation technique the substrate and liquid crystal material are dissolved in a solvent. The solvent is then removed by evaporation or some other process at a controllable rate to begin phase separation. Droplets begin to form as the encapsulating substrate and liquid crystal come out of solution and the droplet formation ceases when all the solvent is evaporated or otherwise removed.

FIGS. 4E and 4F provide a schematic illustration of the non-transmission state/transmission state for a cell of an active mask having substrate dispersed liquid crystal layer or component 220. As shown in FIG. 4E, unpolarized light (e.g., unpolarized UV electromagnetic radiation) is directed at mask 22'. If no electric field is applied as shown in FIGS. 4E and 4G, the bubbles or droplets of liquid crystal material take on many different orientations. Since at least one of the two indices of refraction of the liquid crystal material in bubbles 225 and the indux of refraction of the substrate must differ, there will be a scattering of light which renders the pertinent matrix cell substantially non-transmissive to the incoming energy.

Upon the application of an electric field as shown in FIGS. 4F and 4H the director of the liquid crystal material will become aligned with the electric field. With the index of refraction of the liquid crystal material (for electromagnetic radiation coming in perpendicular to the electric field generated director direction) matching the index of refraction of the substrate, the applied electromagnetic energy will propagate all the way through the mask so as to place the pixel segments with an electric field generated there across in an energy transmission state. Thus, by controlling (e.g., control means featuring a processor/interface for controlling which pixel cells have an electric field across and which ones do not) the transmission states of the substrate dispersed material within predetermined pixel cell regions can be adjusted to achieve a desired transmission pixel pattern. Thus, when the electromagnetic radiation applied to the transmission mask is ultraviolet radiation and the pixels are arranged in a predetermined pixel transmission pattern through use of the electric field generator, a corresponding ablation pattern can be imposed on a desired substrate.

Because of the random orientation of the thousands of bubbles dispersed within the substrate, some degree of electromagnetic radiation will typically be able to make it through a single layer mask. For situations wherein full blockage in the non-transmission mode is desirable such as in the aforementioned opthalmological, photoresist, microelectronics and photolithography fields from the standpoint, for example, more exact energy application at the desired locations on the substrate, a plurality of individual substrate dispersed liquid crystal layers or sections are arranged in a stacked (preferably monolithic) arrangement for further transmission control over the incoming electromagnetic energy. This can include, for example, a plurality of cells such as shown in FIG. 4D in series with respect to the optical path or, as explained in greater detail below, a single cell with multiple substrate-dispersed liquid crystal layers and suitable deposited electrode layers and support substrates.

Figure 4J:
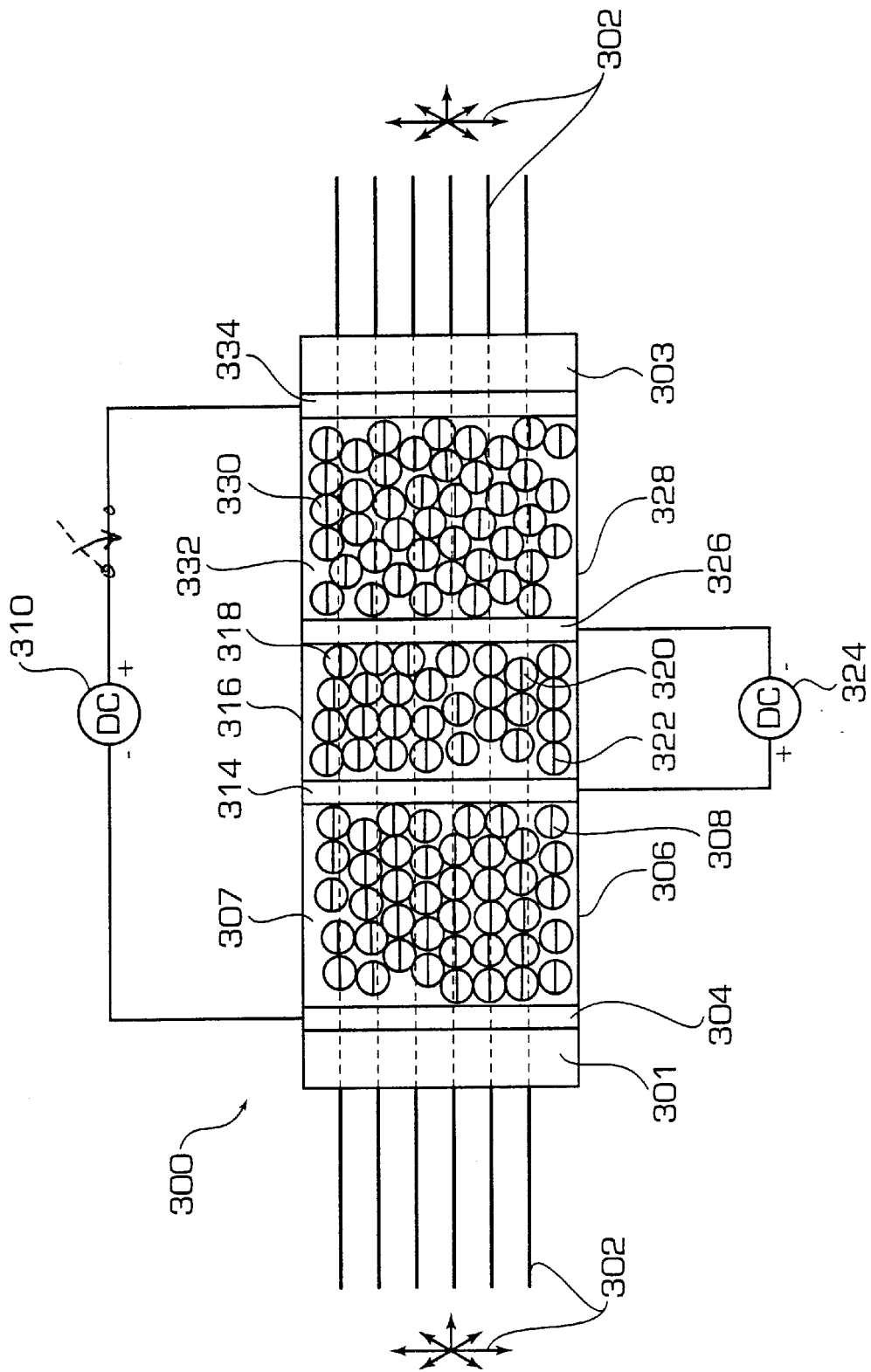
FIG. 4J illustrates unpolarized light that is transmitting through the mask cell made possible upon the application of a small voltage to the external electrodes on the triple substrate-dispersed liquid crystal so as to align the directors of the bubbles in the two outer substrate-dispersed liquid crystal layers with those of the intermediate substrate-dispersed liquid crystal layer or component with pre-set electric field.
Figure 4K:
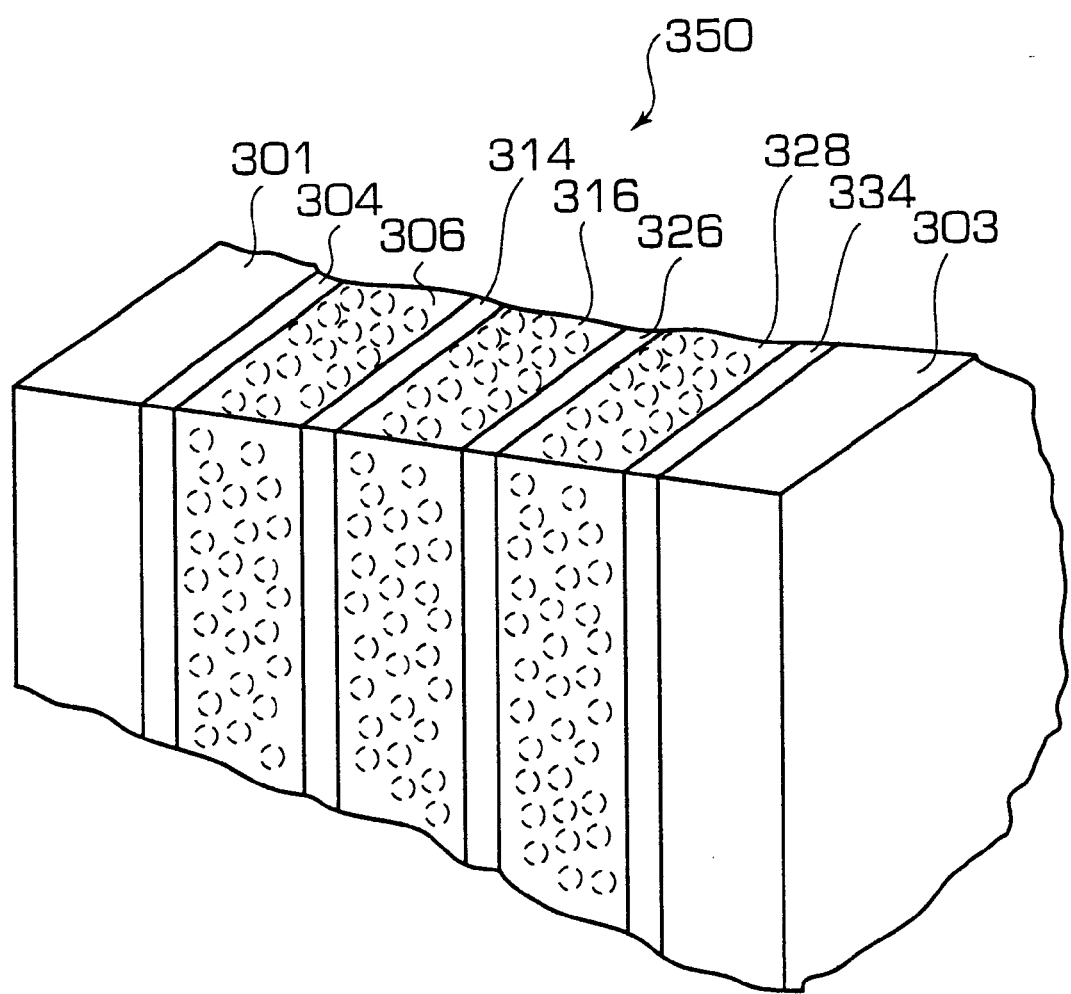
FIG. 4K shows a mask segment or a segment of an electo-optical device with a multi-stack of substrate-dispersed liquid crystal material layers with outer substrate support plates and sandwiched electrode layers.

Reference is now made to FIG. 4I, 4J and 4K which illustrate a preferred multi-stack substrate-dispersed liquid crystal cell 300 (forming a pixel cell segment of an active mask such as active mask 22) designed for full transmission blockage of electromagnetic energy applied from, for example, laser beam 10 in the system of FIG. 1.

FIG. 4I schematically illustrates cell 300 when in an "off" or non-transmission state. As seen in FIG. 4I, incoming unpolarized electromagnetic energy 302 (e.g., ultraviolet energy such as that output by an excimer laser with for example, a wavelength of 193 nm) passes through a first UV grade support substrate 301 and then through the transparent first deposited electrode layer 304 whereupon it passes into first substrate dispersed liquid crystal layer 306 having randomly oriented liquid crystal bubbles (i.e., the liquid crystal directors of bubbles 308 being randomly distributed due to voltage source 310 being in an off state) within substrate 307.

As shown, because of the random orientation of the directions in bubbles 308 within the encapsulating substrate 307 the incoming electromagnetic radiation is then scattered as represented by FIG. 4I whereupon a substantial amount of the energy is blocked. Due to the random orientation, some electromagnetic radiation might pass through second deposited electrode layer 314 and into second, intermediate substrate-dispersed liquid crystal layer or cell component 316 having liquid crystal bubbles 320 dispersed within encapsulating substrate 318 (preferably 318 and 320 correspond material wise with 308 and 307). The directors 322 are oriented perpendicular to the electromagnetic confronting face of the cell due to the electric field generated by electric field generator 324.

For any rays making it through layer 306, their direction will be such that their angle of reelection will result in their further deflection within the intermediate cell 316. This arrangement will orient any such random leakage ray so as to prevent energy from transmitting through cell 316 and out through the next in line deposited electrode layer 326 and a further blocking cell component which is shown as dispersed liquid crystal layer 328, such that all or essentially all of the transmitted energy is not allowed through third substrate-dispersed liquid crystal layer 328 (comprised of randomly oriented bubbles 330 within substrate 322) and the fourth in line deposited electrode layer 334. As with substrate-dispersed liquid crystal (e.g., an electropolymer dispersed layer) 306, layer 328 has random bubbles ad voltage source 310 is in a non-electric field generation state. FIG. 4I also illustrates first and second substrate plates 301 and 303 which are preferably formed of UV grade synthetic fused silica (UV GSFS ($SiO_2$)).

FIG. 4J illustrates cell 300 in a transmission "on" state wherein unpolarized electromagnetic energy 302 (entering in a common direction with respect to the below described aligned directors of each bubble set) passes freely through cell 300 to a desired projected surface (e.g., the cornea of an eye). As shown in FIG. 4J, in addition to voltage source 324 continuing to maintain intermediate layer or cell component 316 with the directors of bubbles 320 oriented in the desired direction of travel of the electromagnetic energy beam 302, voltage source 310 is placed on such that the directors in bubbles 308 in layer 312 and the directors in bubbles 330 become commonly oriented with the directors in bubbles 320 in intermediate layer 316. Thus, with this arrangement, the electromagnetic radiation (e.g., a pulsed excimer laser output) is free to pass through toe achieve a desired ablation effect on a substrate to be ablated.

FIG. 4K illustrates mask 22 segment 350 (a similar segment as represented in FIG. 3A for the electrochromic and FIG. 4D for the single layer substrate disposed embodiment) which corresponds with the multi-stack (or multi-series) arrangement described above for FIGS. 4I and 4J. As shown in FIG. 4K there is provided first substrate plate 301 of, for example, UV grade synthetic fused silica. This UV transparent substrate plate is followed by first transparent voltage electrode layer 304 and then by first substrate dispersed liquid crystal material layer 306.

Also shown in FIG. 4K is second electrode (e.g., ITO) layer 314 followed by second substrate-dispersed liquid crystal layer 316 (which is materially subjected to an electric field in FIG. 4J), then third electrode layer 326 and then third substrate dispersed liquid crystal layer 328. Second support plate 303, (which preferably corresponds with last support plate 301) is placed so as to sandwich the fourth electrode layer 334 between it and layer 328. While FIG. 4K features a monolithic unit, a series of individual and self contained mask plates could be used which together achieve the added blocking function described with respect to FIGS. 4I and 4J.

In addition to the aforementioned ablation system, the above-described controlled (preferably dual control of intermediate and outer substrate-dispersed layers) multi-stack or multi-series substrate (e.g., polymer) dispersed liquid crystal mask also has utility for other uses including, for example, use in the visible electromagnetic radiation spectrum such as for optical displays, projectors, screens, windows, shutters, rear view mirrors and other optical blocking/transmission devices or applications.

With reference now to FIGS. 7, 8A to 8F and 9A–9F, a discussion of a preferred ablation sequence involving ablating volumetric ablation segments from an exposed cornea to achieve a desired cornea sculpturing (e.g., a LASIK procedure) using the matrix system 102 (FIG. 1) in conjunction with a laser system such as laser system 100 (FIG. 1) and one of the above described mask embodiments of the present invention is described. For simplifying the discussion, the pixels 125 (FIG. 6) in array 122 (FIG. 5) will be treated as each having either a fully "on" (100% duty cycle) or a fully "off" (0° duty cycle) state in accordance with each matrix reconfiguration being made to coincide with the master pulse sequence of the excimer laser beam such that the array changes once between each pulse and each pixel cell is maintained fully on or off with a given array for the full pulse period.

In other words, each pixel is maintained on for the full pulse period rather than switching a transmitting pixel to a blocking state at some point prior to completion of the pulse duration. Also, with respect to FIGS. 8A to 8F, and in similar fashion to the presentation in FIG. 3A, the pixel grouping(s) which allow for transmission of the laser energy to the exposed corneal are shown by lighter areas 123 in each array depiction 122 while the blocking pixels 125 are shown by darker shading in mask 122 (e.g., by way of electrochromic electro-optical cell or a substrate-dispersed embodiment such as the multi-layer embodiment described above).

FIG. 7 shows a schematic customized volumetric ablation pattern data has been formed such as in a manner described in U.S. patent application Ser. No. 09/267,926 to Dr. Luis Antonio Ruiz which application is incorporated herein by reference. FIG. 1 also shows topographer 50 and aberrometer 52 which are useful either alone or in combination in determining the desired volumetric ablation pattern data set for achieving the desired resultant ablation volume in the cornea. Regular ablation patterns used commonly for myopic, hyperopic, and astigmatism treatment (e.g.,from a library of stored volumetric ablation volume patterns) can also be relied upon (either alone or in combination with different treatment requirements) in forming the desired three-dimensional volumetric ablation volume pattern. In addition, the present mask system and laser system are also well suited for ablations directed at presbyopia correction such as described in U.S. Pat. Nos. 5,533,997; 5,928,129; and PCT/US99/26242 each to Dr. Luis Antonio Ruiz and each incorporated herein by reference.

While the borders of clear regions 123 (e.g., FIG. 8A) are shown as being entirely smooth curvatures there would be some degree of stepped edging (e.g., scalloped stepped edging if circular pixels are used) in view of the pixel array. However, with an n×m pixel array (see FIG. 5) of, for example, 512×512 cells and with each preferably being square shaped with $100\mu$ sides a very fine resolution peripheral contour would be formed in any ablated material.

FIGS. 8A to 8D show six different matrix array patterns that are each set based on a switch over time period (in this embodiment, the matrix switch time is made in one-to-one correspondence with the pulse duration of the laser). As shown by FIGS. 8A and 9A the pixel array is set so as to remove the volume of material lying above reference line T1 (FIG. 7) during a first laser pulse of the polarized large beam. FIG. 8A shows the pixel matrix array setting (e.g., an array of 1024×1024 with a $100\mu$ square size) for achieving the ablation volume removal segment lying above reference line T1. FIG. 9A shows a schematic presentation of an ablation segment that would be removed following a laser beam pulse application through the mask and to the projected surface.

FIG. 8B shows the pixel matrix array setting for achieving the ablation volume removal segment (predetermined by processor 32 following receipt of the overall desired volumetric ablation volume pattern data for the cornea being ablated as in the segment above T1) lying between reference lines T1 and T2 in FIG. 7. FIG. 9B illustrates schematically the cumulative effect of removal of the of ablation volume segments by the laser beam for two setting cycles of the matrix array. Similarly, FIG. 8C shows the pixel matrix array setting for achieving the ablation segment lying between reference lines T3–T2 with FIG. 9C showing the cumulative volumetric effect of the three represented different pixel matrix array settings. Pair sets 8D–9D; 8E–9E; 8F–9F show additional matrix array settings and the corresponding cumulative volumetric ablation following application of the laser beam pulse with FIG. 8D directed at the ablation segment defined between reference lines T4–T3, FIG. 8E directed at the ablation segment defined by reference lines T5–T4, FIG. 8F directed at the ablated segment defined by reference lines T6–T5 The ablation segment T7–T6 in FIG. 7 is represented by the pixel pattern 123 shown in FIG. 3A with the stacked ablation segments lying above the best clinical sphere (representation BS in FIG. 7) intended to correspond with the topographical plan view of the three dimensional volumetric ablation pattern represented in FIG. 3C taken along cross-section lines 7—7 in FIG. 3C. The best clinical sphere BS shown in FIG. 7 represents the desired final, resculptured profile for the exposed cornea believed to be best suited for that particular patient such as by way of the technique explained in the aforementioned U.S. patent application Ser. No. 09/267,926 filed Mar. 10, 1999 by Dr. Luis Antonio Ruiz.

As can be seen from a comparison of FIGS. 8A–8F, for this volumetric ablation volume pattern being removed, the volumetric ablation segments expand and merge together in going from a removal of the outer exposed corneal topographical (z-axis) extremities toward the predetermined best clinical sphere BS reference line (in cross-section) lying below the irregularities. As the laser pulse applications are cumulative, the sequence of pattern settings could be altered (e.g., starting with the configuration of FIG. 8F and working in reverse and working in sequence back to 8A or even a mixed application of array sets 8A to 8F).

Also, while FIG. 7 shows an (over exaggerated for ease in viewing) extension of cornea tissue in a central region above the best clinical sphere, reference line BS could also represent the initial outer exposed cornea surface profile wherein a series of ablations, based on conventional, preestablished volumetric ablation profiles such as in correcting myopia, hyperopia and astigmatism (or presbyopia as discussed above are ablated), are performed. For instance, generally circular, centralized ablation segments can be imposed upon the cornea to achieve a conventional corrective myopic central cap reduction in the center region of the cornea, but with very smooth surfaces and high precision, while avoiding the degrading effect of overlapping and the time delay associated with an overlapping flying spot technique). Also, as a typical ablation depth for an excimer laser pulse is $0.25\mu$, the number of ablation stacks would generally be much larger in number than the schematic representation in FIGS. 8A–8F (e.g., a number in the few hundreds corresponding with the aforementioned number of large spot laser beam pulses typically required to achieve typical diopter corrections).

Thus, upon completion of the preset number of different pixel array settings and laser pulse applications following the mask resettings or refreshings, a removed volumetric ablation pattern conforming to the predetermined volumetric ablation pattern determined by an analysis of the eye is achieved with high precision like a flying spot laser but with the avoidance of the time delays and overlapping problems associated with a flying spot laser. In addition, there is provided a multi-use mask which can be used for handling a plurality of different patient ablation requirements while using a speedier large beam application; but without the complexities of the previous mechanical fixed mask arrangements or the erodible masks of the prior art. Moreover, the laser system of the present invention provides for high resolution, extremely smooth walls and avoids ridge and valley formation due to excessive overlap.

Figure 14:
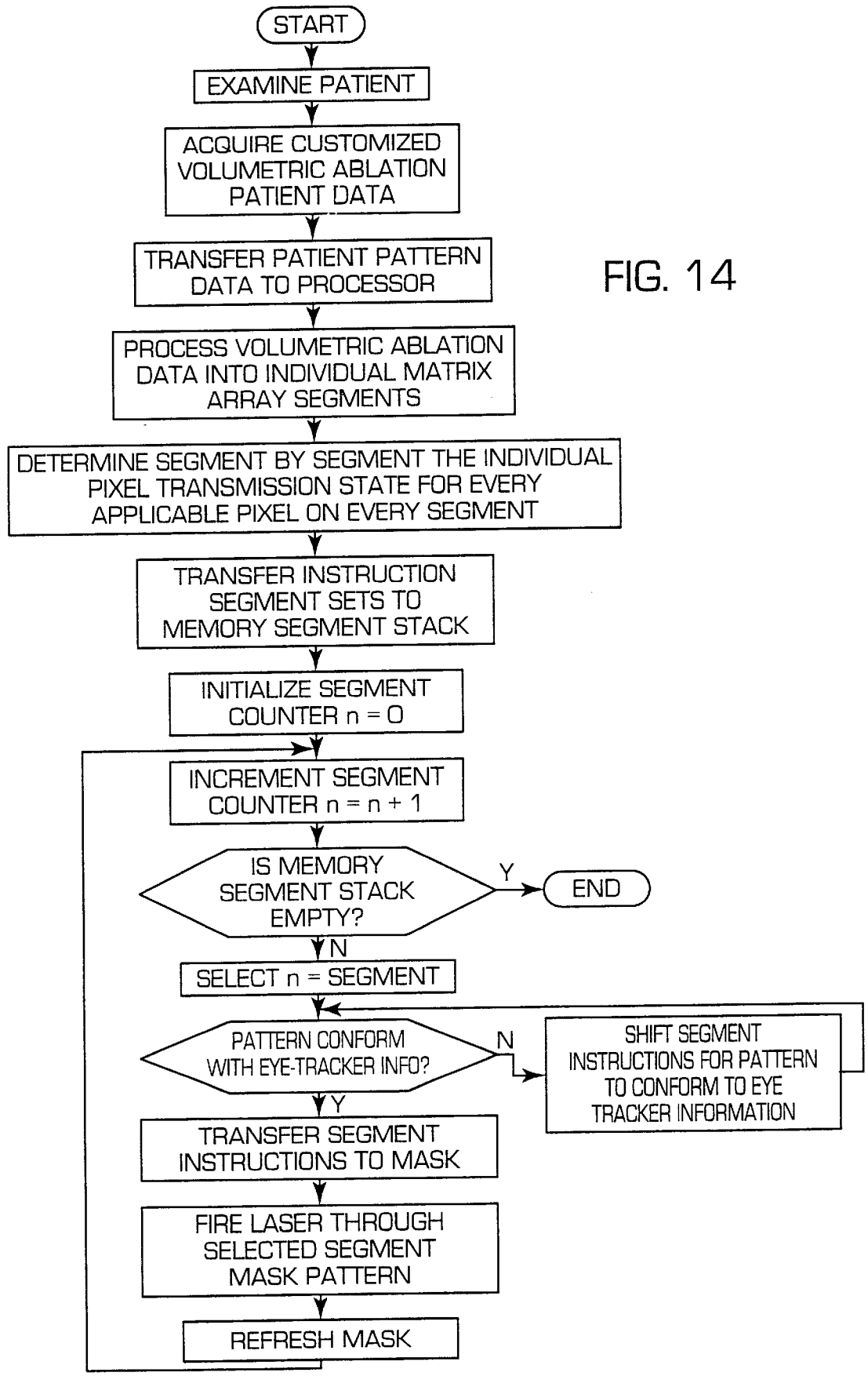
FIG. 14 provides a flow diagram of a method of utilizing the laser system of the present invention for performing a controlled ablation on a substrate.

FIG. 14. provides a flow chart illustrating a sequence of steps in carrying out a volumetric ablation removal technique such as that represented by FIGS. 8A to 8F. In a preferred initial step, the substrate to be ablated (e.g., the cornea of a patient which is a representative substrate presented as an example in FIG. 14) is examined to determine what type of ablation requirements might exist. If a preestablished ablation sequence on a substrate that does not appreciably vary from substrate to substrate is involved, this step can be skipped. In the context of eye laser surgery, an applicable volumetric ablation pattern data set is subsequently formed or acquired which best suits the individual needs of the patient. Reference is again made to U.S. Ser. No. 09/267,926 which discusses in additional detail some of the various concerns and some of the applicable techniques for acquiring an ablation pattern data set, although any other conventional technique for determining desired ablation volumes to be ablated can be utilized under the present invention.

The volumetric ablation pattern data set is acquired for the ablation deemed best suited for the patient (48) (e.g., a matrix of x, y, z values conforming to the volume of cornea lying between a best clinical sphere and the analyzed topography of the cornea and/or the volume based on aberrometer determined characteristics of the different optical components and shapes of the eye by, for example, use of topographer (50) and/or aberrometer (52)). This information is sent to a suitable processor such as main computer 32. In a preferred embodiment, the received data set is broken down into volumetric ablation segments which preferably conform to a predetermined laser ablation depth defined by the laser characteristics and the laser energy densities utilized. This can be seen in a review of FIG. 7 which illustrates, in schematic fashion, stacked individual volumetric ablation segments which, in the cumulative, remove with high precision the ablation volume defined by the acquired volumetric ablation pattern data fed to the processor.

The processor then determines, for each volumetric ablation segment, the desired individual pixel array settings required to satisfy the desired volumetric ablation segment profile for the applicable ablation segment. For example, with an x, y, z corneal topograph matrix data set as the acquired customized volumetric ablation pattern data, the processor, based on the maximum and minimum z-axis points in the data set, determines the maximum distance (MD) FIG. 7 between the same points and, based on the ablation characteristics of the laser beam (maximum ablation depth) (LD), breaks down the maximum distance (MD) into a number (N) of z-axis ablation segments that corresponds to the formula MD=LD×N with N equal to the pulses×the duty cycle ration (which is 1:1 for the above described embodiment).

With a typical corneal laser ablation depth of $0.21\mu$ to $0.25\mu$ and a preferred pixel window of between 100 to $150\mu$ (per side) a very high precision capability is attained both with respect to ablation depth and with respect to peripheral or x-y plane boundary profiling. With an ablation depth value of $0.21\mu$ or $0.25\mu$ and pixel size of $100\mu$ to $125\mu$ per side, it is possible to achieve under the present invention a resolution of, for example, ⅕₀th of a diopter, extremely smooth ablation surfaces, no (±0.75% with respect to pixel size) overlap or spacing, or essentially no (±1 to 5%) overlap or spacing, and a very high accurate registration between the desired volumetric ablation pattern and the actually ablated volume. Also, because of the very small ablation depth ($0.21\mu$ to $0.25\mu$) each matrix array cycle (preferably in a 1 to 1 ratio with respect to the laser pulse cycle), any deviation (due to N not being a whole number integer) in having MD=LD×N would still allow for higher precision contouring.

As further shown by FIG. 14, after the volumetric ablation data is broken down into individual ablation formation segments, the processor then determines the individual pixel transmission state for every pixel in every segment. For example, a review of the corneal volume representation of the acquired volumetric ablation data set for a chosen matrix array segment is made and the pixel settings for achieving the corneal volume representation is implemented (i.e., setting to "on" those pixels which correspond in location to the matrix array segment for laser beam transmission, while placing all others in the matrix array in a blocking state). While a direct feed following each determination of the required pixel transmission state for an ablation segment to an activated mask is possible, it is preferable to store in a memory stack each individual matrix array data set for each of the individual matrix array segments (also described as an ablation segment). Each matrix array data set is assigned a number and then an ablation process is initiated wherein one of the numbered matrix array data sets is chosen and its information transferred (e.g., through computer interface 34 which transfers, for example, pixel on/off data representations into voltage pulse on/off voltage signals so as to achieve the desired overall pixel state for the matrix array). The laser beam is then fired through the selected, activated mask pixel array and directed on toward the substrate such as the cornea to be sculptured. Preferably the mask is varied between a preexisting state and a new state corresponding with the chosen segment between each pulse and with the "switch over" timing being achieved between laser shots, although it is also possible to carry out a number of pulses on the same matrix array setting prior to switching over to the next matrix array depending on, for example, the z-axis height of each segment. Also, for a sufficiently long laser pulse duration or a continuously applied electromagnetic radiation source, the duty cycle for an "on" pixel can be made less than 100% to accommodate, for example, any relative difference in material to be ablated along a common ablation volume segment's lower reference line. This would alter the number of on/off switch overs per pulse.

Also, in one embodiment of the invention, the resetting of the mask includes first setting all pixels within the array to a common "off" position and then placing those pixels which are to be "on" in an on setting while leaving the other pixels unchanged (or vice versa if the resetting involves switching all to "on" initially). The former arrangement is preferable, as the resetting of all to "off" between the switching over to the next desired array pattern provides an additional safety blocking screen.

In an alternate embodiment, the previous mask setting is maintained and a comparison is made via the processor between the chosen matrix array set and the preexisting matrix array set to determine which pixels require changeover and which can stay the same. This can lessen the number of individual pixel setting changes, particularly in situations wherein the next segment has many pixel settings in common with an earlier setting as in FIGS. 8A–8H illustrating a situation where the later pixel setting segment generally builds upon an earlier setting by expanding out the x-y plane ablation profile pixel representation (or in an opposite matrix array segment processing).

As further shown by FIG. 14, the cycle of switching the matrix arrays from a prior to a new setting and firing the laser is repeated until it is determined that each memory segment has been implemented and that the memory segment stack is empty. The timing between mask refreshings in accordance with a preferred embodiment of the present invention is preferably less than 150 milliseconds (ms) more preferably less than 100 ms and even more preferably less than 50 ms with a range of 25 to 50 ms being well suited for many applications of the present invention. This invention mask refreshing cycle is synchronized with the "on" main laser pulse, also individual pixel cells can be controlled separately within the main laser pulse duration to achieve multiple on/off pixel modes during the laser pulse period and the synchronized refreshing period, if applicable.

As described above, pixels that are in a transmitting state can be left "on" for the full time period of the synchronized laser pulse to achieve the characteristic full ablation depth of the laser beam's pulse. This relationship can be seen by a comparison of FIGS. 15A and 15B wherein the laser pulse duration P is in an on state for the entire main laser pulse period (corresponding with the laser energy passage time period) as represented by the darkened region $R_1$ in FIG. 15B. FIG. 15B represents a 100% duty cycle with respect to the laser pulse period P. On the other hand, a pixel that is maintained entirely in an "off" state (not shown) during the laser pulse period P would thus have a 0% duty cycle (and no pulse representation).

To achieve an intermediate degree of ablation in sub-areas within an ablated segment area during pulse period P, the duty cycle can be varied from pixel to pixel by switching the duty cycle of respective pixels in a present matrix array. For example, FIG. 15C shows a 50% duty cycle where a respective pixel cell is switched from a transmission "yes" state to a transmission "no" state so as to be on for 50% of the pulse period P. In this way a partial ablation is carried out relative to the capability of 100% duty cycle period which is shown in FIG. 15C during the first half of the pulse period but could also be applied during the last half of the pulse period (or refreshing period) or an intermediate period of the pulse period as well to achieve a 50% duty cycle.

FIGS. 15D and 15E illustrate even smaller duty cycles of 25% and 12.5%, respectively. Adjacent each duty cycle pulse presentation, there is schematically illustrated the corresponding ablation depth for that duty cycle.

The upper portion of FIG. 15F schematically illustrates the different ablation percentages made possible during one of the repetitive laser pulse periods, while the lower half shows the corresponding degree of ablation carried out on an underlying substrate. Thus, with a varying of the individual duty cycle within a particular matrix array a variation in depth of ablation can be achieved with respect to the underlying substrate. Whether a duty cycle of less than 100% can be utilized will depend upon the time of the laser pulse period. The duty cycle manipulation would provide advantageous flexibility and precision (considered above and beyond the capability of switching individual voltage levels within the pixels in a given matrix set). This flexibility and added precision being made possible by varying the duty cycle amongst pixels in a particular pixel array set is also applicable to a variety of fields including for example, photoresist and photolithography applications, and with a variety of electromagnetic radiation sources including pulsed or continuously supplied electromagnetic radiation providers such as a xenon lamp, a mercury vapor lamp or the like.

With reference again to FIGS. 1 and 2, some additional preferred features for the eye laser surgery system 100 shown are discussed. To properly focus the exposure of the matrix transmitted laser beam onto the projecting zone, non-ablating lasers are preferably used. For example, two HeNe lasers such as a red HeNe laser (39) with a wavelength of about 632.8 nm and a Green HeNe laser (40) with a wave length of about 543.5 nm, respectively, are preferred for alignment with a third HeNe laser (20) of about 632.8 nm used for patient fixation. As the third HeNe laser is used for patient fixation, it must be aligned with the patient eye and the alignment lasers. Additionally, to accurately control X, Y pattern exposure registration on the patient cornea, an infra-red eyetracker system (36) is used to compensate patient eye movement during an ablation procedure. The eyetracker system monitors the center of the cornea (or some other fixed point) and assures that the UV light beam is precisely projected to the target area of the cornea following any eye movement.

Under the present invention, to achieve correlation between the laser beam application and a patient shifted projecting zone as determined by eyetracker 36, the eyetracker outputs data to a processor such as processor 32 and the shift parameters provided by the eyetracker are processed by the processor and fed to the active pixel array in the form of signals to alter the pixel array pattern (e.g., the pixel cell x-y reference coordinates) whereupon an appropriate shift in the on/off states of the pixel array assigned for producing the latent images for forming the ablation segment is made.

In this way, a deviation in the patient's eye can be accommodated by the present invention, without the need for mechanically moving components which can wear out or jam (each which can produce serious implications in a surgical procedure). While the avoidance of any mechanical moving components is preferred through use of electronic pixel shifting to achieve a shifted transmission configuration in the active mask, the present invention can also include an assembly comprising turning mirror 21, active mask 22, focusing lens 24 can be implemented as a unit with a moveable support so as to keep the center axis of the projected beam at the same location despite the eye movement picked up by the eyetracker (e.g., angular movement together with x-y plane movement of the unit).

Figure 16:
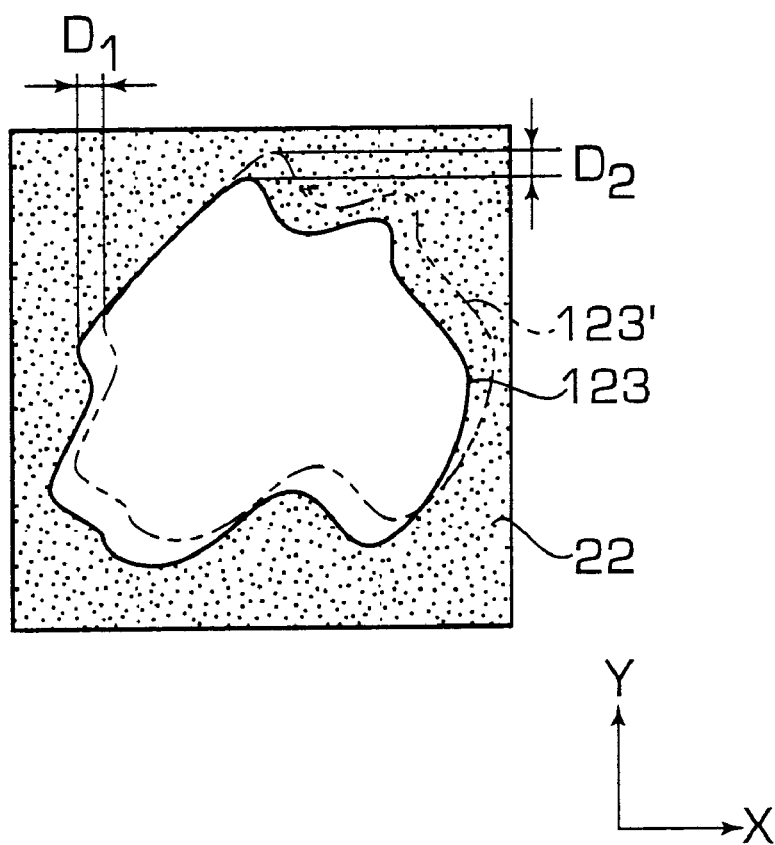
FIG. 16 shows a depiction of electronic active mask compensation on the x, y axis based on a substrate shifting monitoring means such as an eyetracker.

FIG. 16 schematically illustrates a shifting in the mask array pattern to accommodate a shift in the projected zone of a substrate to be ablated with the shifting being measured by substrate monitoring means which conveys shift information to a processor, which in turn controls the mask to initiate a new setting prior to the next energy application. Thus, with respect to a laser system as shown in FIG. 1, the transmission pattern 123 is shifted (in conjunction with a shift determined by the eyetracker 36 and shift information processed by main computer 32 and relayed through interface 34) to new pattern position 123' or mask 22 (includes 22') to properly place the applied energy on the shifted cornea.

FIG. 16 also shows lengths D1 and D2 representing shifting distances in the image presented by the mask along the x-y plane of the matrix 22. If D1 or D2 exceed a preset standard (e.g., a shift beyond a 3 to 5 mm acceptable outer limit range on the main computer) the processor can initiate a laser shut down through use of beam shutter 14. A substrate monitoring device similar in function can also be used for situations where the substrate is subject to movement (e.g., a heavy vibration environment with regard to the substrate).

FIGS. 1 and 2 illustrate the use of a video camera system (37) provided to show the patient's eye in a color monitor (38). Initial positioning of patient is realized by a microprocessor controlled bed (46) that responds to commands generated by a joystick (44) which moves the patient bed on the axes X, Y and Z and interlocks the patient bed when the surgery is in progress. The patient bed is also interfaced with the main computer via computer interface (42). As earlier noted, prior to surgery, the patient (48) is accurately examined by a topographer (50) or an aberrometer (52) or any other type of medical device for analyzing the optical structure of the eye, and the information generated by the analyzer is then transferred to the main computer (32) which executes a software and generates the customized cornea ablation pattern deemed best suited by the surgeon for achieving the desired correction. The analyzer of the eye characteristics information can be a component of the overall system or can be a remote sub-system with the volumetric ablation pattern data set deemed best suited for that patient being stored by the main computer either by way of a direct feed to the main computer from the analyzer or stored on an appropriate storage medium for transfer to an input of the main computer, or transferred remotely from one location to another through any suitable information transmission means such as a telephone line.

Although the present invention has been described with reference to preferred embodiments, the invention is not limited to the details thereof. Various substitutions and modifications will occur to those of ordinary skill in the art following a review of this application, and all such substitutions and modifications are intended to fall within the spirit and scope of the invention as defined in the appended claims.

What is claimed is:

1. A patternable mask system for controlling the transmission of electromagnetic radiation, comprising:
a patternable electro-optical mask having a plurality of individual pixel cells with individually adjustable states of transmission with respect to electromagnetic radiation, and said pixel cells including electrochromic material.

2. The mask system of claim 1 further comprising a processor interfaced with said patternable mask for controlling relative transmission states between the individual electrochromic material pixel cells.

3. The mask system of claim 1, further comprising a beam expander/collimator assembly positioned upstream, with respect to the electro-optical mask.

4. The mask system of claim 3 wherein said electrochromic material is supported by a UV grade substrate for the passage of UV electromagnetic radiation to the electrochromic material of the pixel cells of said mask.

5. The mask system of claim 4 further comprising a focusing lens positioned downstream, with respect to UV electromagnetic radiation travel, of the electrochromic material.

6. The mask system of claim 1 wherein said pixel cells are formed from an outer pair of UV grade substrates, a pair of electrode layers and a solid layer of electrochromic material sandwiched between the electrode layers.

7. The mask system of claim 6 wherein said UV grade substrate is a material selected from a group consisting of UV grade synthetic fused silica, sapphire and quartz.

8. The mask system of claim 1 further comprising a processor interfaced with said mask for controlling relative transmission states between said individual pixel cells for forming a transmission pattern, and said processor comprising means for shifting a pattern formed in said mask in conjunction with a shift in a substrate to receive electromagnetic energy transmitted through said mask.

9. The mask system of claim 1 wherein said pixel cells include a UV grade support substrate designed for receipt of unpolarization UV electromagnetic radiation at a 193 nm wavelength.

10. The mask system of claim 1 wherein said mask involves a pixel array having at least 512×512 resolution with pixel size of 100$\mu$ or less.

11. The mask system of claim 10 wherein said resolution is at least 1024×1024 in number.

12. The mask system of claim 1 wherein said individually adjustable states of transmission are limited to maximum transmitting on and maximum blocking off.

13. The mask system of claim 1 wherein said mask is designed for receipt of laser pulses and said mask system further comprises pixel switching timing means for timing pixel switching between different pixel states that is in a one-to-one relationship with respect to laser pulses received by said mask.

14. The mask assembly of claim 1 wherein said mask further comprises pixel switching timing means for timing individual pixel switching between different states and which switching timing means sets a duty cycle for individual pixels at 0% to 100% with at least one set duty cycle being at an intermediate value falling between 0 to 100%.

15. A patternable mask system for controlling the transmission of electromagnetic radiation, comprising:

a patternable electro-optical mask having a plurality of individual pixel cells with individually adjustable states of transmission with respect to electromagnetic radiation, and said pixel cells including substrate-dispersed liquid crystal material having a substrate material encapsulating dispersed liquid crystal bubbles or droplets.

16. The mask system of claim 15 further comprising a processor interfaced with said patternable mask for controlling relative transmission states between the individual substrate-dispersed liquid crystal material pixel cells.

17. The mask system of claim 15, further comprising a beam expander/collimator assembly positioned upstream, with respect to the electro-optical mask.

18. The mask system of claim 17 wherein said mask is a solid state, monolithic member having multiple layers of substrate-dispersed liquid crystal layers.

19. The mask system of claim 18 further comprising a focusing lens positioned downstream, with respect to UV electromagnetic radiation travel, of the substrate-dispersed liquid crystal material.

20. The mask system of claim 15 wherein said mask is comprised of an outer pair of UV grade support substrates, a pair of electrode layers and a solid layer of substrate-dispersed liquid crystal material.

21. The mask system of claim 20 wherein UV grade support substrate is a material selected from a group consisting of UV grade synthetic fused silica, quartz or sapphire.

22. The mask system of claim 1 further comprising a processor interfaced with said mask for controlling relative transmission states between said individual pixel cells and said processor comprising means for shifting a pattern formed in said mask in conjunction with a shift in a substrate to receive electromagnetic energy transmitted through said mask.

23. The mask system of claim 15 wherein said mask comprises a pixel cell with multiple substrate-dispersed liquid crystal material members with an electrode layer disposed between said members.

24. The mask system of claim 23 comprising pixel cells having in series, a first electrode, a first substrate dispersed liquid crystal member, a second electrode, a second substrate-dispersed liquid crystal member, a third electrode, a third substrate-dispersed liquid crystal layer and a fourth electrode.

25. The mask of claim 24 further comprising electric field generating means for maintaining an electric field across said second substrate dispersed layer and for switching between a no-electric field state for said first and third substrate-dispersed layers and an on electric field state for said first and third substrate-dispersed layers so as to place said first, second and third substrate-disperse layers in a transmission state while an electric field is being applied across said second substrate dispersed layer.

26. The mask system of claim 15 wherein said pixels are arranged in an array at least 1024×1024 in number and with each pixel having a maximum $100\mu$ side length or less.

27. The mask system of claim 15 wherein said mask is designed for receipt of laser pulses and said mask system further comprises pixel switching timing means for timing pixel switching between different pixel states that is a one-to-one relationship with respect to laser pulses received by said mask.

28. The mask assembly of claim 15 wherein said mask further comprises a pixel switching timing means for timing individual pixel switching between different states and which switching timing means sets a duty cycle for individual pixels at 0% to 100% with at least one set duty cycle being at an intermediate value falling between 0 to 100%.

29. An electro-optical device, comprising, with respect to electromagnetic radiation travel, in series:

a first electrode, a first substrate-dispersed liquid crystal member, a second electrode, a second substrate dispersed liquid crystal member, a third electrode, a third substrate dispersed liquid crystal member, and a fourth electrode.

30. The electro-optical device as recited in claim 29 further comprising electric field generating means which maintains an electric field across said second substrate-dispersed liquid crystal member and which provides means for switching between on and off electric field states for said first and third substrate-dispersed liquid crystal members.

* * * * *